(12) United States Patent  (10) Patent No.: US 7,781,633 B2
Vaughn et al.  (45) Date of Patent: Aug. 24, 2010

(54) METHOD FOR CONVERTING AN OXYGENATE FEED TO A LIGHT OLEFIN

(75) Inventors: Stephen N. Vaughn, Kingwood, TX (US); Keith H. Kuechler, Friendswood, TX (US); Thomas H. Colle, Houston, TX (US); Teng Xu, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 721 days.

(21) Appl. No.: 11/810,032

(22) Filed: Jun. 4, 2007

(65) Prior Publication Data

US 2007/0260096 A1 Nov. 8, 2007

Related U.S. Application Data

(63) Continuation-in-part of application No. 10/227,907, filed on Aug. 26, 2002, now Pat. No. 7,227,048.

(60) Provisional application No. 60/345,420, filed on Dec. 31, 2001.

(51) Int. Cl.
*C07C 1/20* (2006.01)
(52) U.S. Cl. ...................... 585/640; 585/639
(58) Field of Classification Search ............... 585/639, 585/640
See application file for complete search history.

(56) References Cited

U.S. PATENT DOCUMENTS 4,440,871 A 4/1984 Lok et al.
4,499,327 A 2/1985 Kaiser
4,547,616 A 10/1985 Avidan et al.
4,873,390 A 10/1989 Lewis et al.
6,023,005 A 2/2000 Lattner et al.
6,137,022 A 10/2000 Kuechler et al.
2003/0109765 A1 6/2003 Fung et al.
2003/0125598 A1 7/2003 Chisholm et al.
2005/0176579 A1 8/2005 Fung et al.

OTHER PUBLICATIONS

Soundararajan, S. et al., "*Modeling of Methanol to Olefins (MTO) Process in a Circulating Fluidized Bed Reactor*," Fuel, vol. 80, pp. 1187-1197 (2001).
Bos, A.N. Rene et al., "*Conversion of Methanol to Lower Olefins. Kinetic Modeling, Reactor Simulation, and Selection*," Ind. Eng. Chem. Res., vol. 34, pp. 3808-3816 (1995).

(Continued)

*Primary Examiner*—Thuan Dinh Dang
(74) *Attorney, Agent, or Firm*—Kevin M. Faulkner; David M. Weisberg; Melinda R. Michalerya

(57) ABSTRACT

The present invention relates to a method for converting a feed including an oxygenate to a product including a light olefin. In particular, this invention relates to converting an oxygenate feedstock with a silicoaluminophosphate catalyst to a product including a light olefin in a reaction apparatus. More particularly, this invention provides a means by which an optimum level of coke can be determined and utilized to generate an optimum or near-optimum yield of light olefins such as ethylene and propylene in a oxygenates to olefins system.

3 Claims, 3 Drawing Sheets

OTHER PUBLICATIONS

Dahl, Ivar M. et al., "*Structural and chemical influences on the MTO reaction: a comparison of chabazite and SAPO-34 as MTO catalysts,*" Microporous and Mesoporous Materials, vol. 29, pp. 185-190 (1999).

Wilson, S. et al., "*The characteristics of SAPO-34, which influence the conversion of methanol to light olefins,*" Microporous and Mesoporous Materials, vol. 29, pp. 117-126 (1999).

Chen, De et al., "*The effect of crystal size of SAPO-34 on the selectivity and deactivation of the MTO reaction,*" Microporous and Mesoporous Materials, vol. 29, pp. 191-203 (1999).

Lewis, Jeffrey M.O. "*Methanol to Olefins Process Using Aluminophosphate Molecular Sieve Catalysts,*" Catalysis, vol. 38, 199-207 (1987).

Holmen, A. et al., "*Natural Gas Conversion,*" Studies in Surface Science and Catalysis, vol. 61, 421-427 (1991).

us 7,781,633 B2

METHOD FOR CONVERTING AN OXYGENATE FEED TO A LIGHT OLEFIN

CROSS-REFERENCE TO RELATED APPLICATIONS

This application claims priority as a continuation-in-part to U.S. patent application Ser. No. 10/227,907, filed Aug. 26, 2002, now U.S. Pat. No. 7,227,048, which, in turn, claims the benefit of U.S. Provisional Patent Application No. 60/345,420, filed Dec. 31, 2001, the entire disclosures of both of which are hereby incorporated by reference herein.

FIELD OF THE INVENTION

The present invention relates to a method for converting a feed including an oxygenate to a product including a light olefin.

BACKGROUND OF THE INVENTION

The production of ethylene and propylene, herein referred to as "light olefins," is typically conducted at very large scales to achieve efficient economy of operation. The conversion of oxygenates to olefins (OTO) and more specifically, methanol to olefins (MTO), has been a subject of great interest in the emerging field of olefin production. The OTO and MTO processes typically use molecular sieve catalysts, especially silicoaluminophosphate (SAPO) molecular sieves.

One goal during the conversion of oxygenates to olefins is to maximize the production of light olefins, preferably ethylene and propylene, and to minimize the production of methane, ethane, propane, and C5+ materials. Increasing the selectivity of preferred hydrocarbon products such as ethylene and/or propylene from the conversion of an oxygenate using a molecular sieve catalyst composition is described in U.S. Pat. No. 6,137,022, and PCT WO 00/74848 published Dec. 14, 2000, which are all herein incorporated by reference.

Production of ethylene and propylene reaches a maximum when a certain level of coke is maintained on the catalyst. U.S. Pat. No. 6,023,005, incorporated herein by reference, teaches the desirability of providing carbonaceous deposits, or coke levels, for oxygenates to olefins conversion processes, in the range of 2 wt % to about 30 wt %, based on the total reaction volume of coked catalyst to promote selectivity to light olefins.

U.S. Patent Application Publication No. 2003/0125598 discloses a process for making an olefin product from an oxygenate-containing feedstock. The application disclosure introducing regenerated catalyst particles into a reaction zone to provide a catalyst mixture in an amount sufficient to provide an average coke loading on the catalyst mixture.

SUMMARY OF THE INVENTION

The present invention solves the current needs in the art by providing an improved method for converting a feed including an oxygenate to a product including a light olefin, in particular by operating in a regime where catalyst coke content is more closely optimized.

One aspect of the invention relates to a process for converting oxygenates to olefins comprising the steps of: a) contacting a feed comprising an oxygenate with a catalytically effective amount of molecular sieve catalyst under conditions effective to selectively convert at least some of the oxygenate to a product comprising prime olefins and depositing a certain amount of coke on the catalyst, the catalyst having an Si/Al$_2$ value, a maximum POS, and an active fraction comprising a number of acid sites; and b) optimizing the POS by adjusting the amount of coke present relative to the number of acid sites contained in the active fraction of the catalyst.

Another aspect of the invention relates to a method for optimizing a coke level for catalysts with different acidity levels comprising the steps of: a) contacting a feed comprising an oxygenate with a catalytically effective amount of molecular sieve catalyst under conditions effective to selectively convert at least some oxygenate to a product comprising prime olefins and depositing an amount of coke on the catalyst, the catalyst having an active fraction comprising a number of acid sites at maximum product selectivity; b) determining the number of carbon atoms per acid site at maximum product selectivity; c) determining a ratio necessary to achieve an optimum selectivity to the product using the equation: carbon atoms per acid site at maximum product selectivity=−51.226*[Si/Al2 in sieve]+25.777; and d) adjusting the amount of coke present on the coked catalyst relative to the carbon atoms per acid sites at maximum product selectivity calculated in step (c). In one embodiment, the method can further comprise the step of operating an oxygenates-to-olefins conversion reactor in such a way as to load an optimum amount of coke on a catalyst, based on an acid site density of the catalyst, to achieve a prime olefin selectivity of at least within 3% of an optimum prime olefin selectivity.

Another aspect of the invention relates to a process for forming a polymer product from an olefin product comprising one or more prime olefin monomers, the process comprising: a) providing an olefin product formed according to any of the processes/methods described herein, which product comprises one or more prime olefin monomers; and b) contacting at least one of the prime olefin monomers, and optionally one or more comonomers, with a catalytically effective amount of a polymerization catalyst under conditions sufficient to polymerize the olefin product and optional comonomer(s).

Another aspect of the invention relates to a process for forming an oligomer product from an olefin product comprising one or more prime olefin monomers, the process comprising: a) providing an olefin product formed according to any of the processes/methods described herein, which product comprises one or more prime olefin monomers; and b) contacting at least one of the prime olefin monomers, and optionally one or more comonomers, with a catalytically effective amount of an oligomerization catalyst under conditions sufficient to oligomerize the olefin product and optional comonomer(s).

DETAILED DESCRIPTION OF THE PREFERRED EMBODIMENTS

Figure 1:
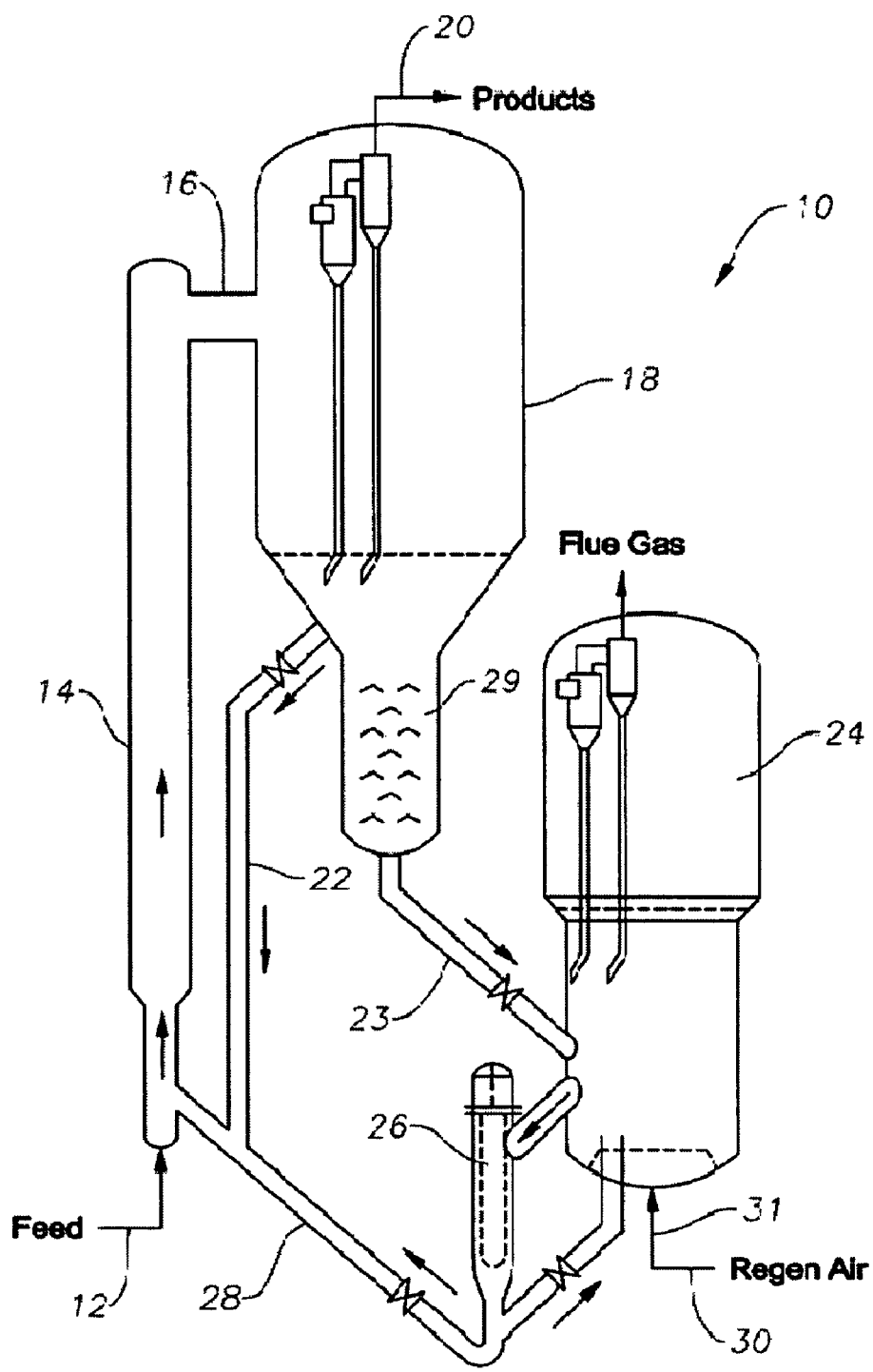
FIG. 1 provides a diagram of a reactor apparatus comprising a high velocity fluid bed with catalyst recirculation, and a regenerator suitable for use in accordance with a preferred embodiment of the present invention.

In an embodiment, an OTO process is provided which maximizes the production of light olefins, preferably ethylene and propylene, and minimizes the production of methane, ethane, propane, and $C_5+$ materials. The average coke loading of the catalyst is maintained in a range particularly selective for producing ethylene and propylene. Such range is based on the acid site density of the molecular sieve component of the catalyst. In other words, these preferred results do not depend solely on maintaining an average coke level. Rather, the preferred light olefin selectivity results from regulating the catalyst's coke level in a range that depends on the particular acidity of the molecular sieve(s) in the catalyst. It has been discovered that there is a direct interaction between the coke content, acid site density and optimum selectivity. A correlation has been developed to allow selection of the optimal coke content. As used herein, prime olefin selectivity (POS), refers to the selectivity for ethylene and propylene.

It has been discovered that the amount of optimum coke on the catalyst varies depending on the type of SAPO utilized and its particular Si content. It would be desirable to discover the relationship between the coke on catalyst level and acid site density (ASD) of the particular catalyst. Additionally, it would be desirable to be able to calculate the optimal coke level for sieves with different acidity levels. It would also be advantageous to identify the optimum coke-to-acid site ratio regardless of knowing the Si content.

It has also been discovered that there is an optimal amount of coke on catalyst for a certain desired product selectivity. More particularly, it has been discovered that the ASD value of a bound sieve can be used to select the proper coke-to-acid site ratio which changes as you change the acidity (or Si content) of the SAPO.

Molecular Sieves and Catalysts Thereof

Molecular sieves suited to use in the present invention for converting oxygenates to olefins have various chemical and physical, framework, characteristics. Molecular sieves have been well classified by the Structure Commission of the International Zeolite Association according to the rules of the IUPAC Commission on Zeolite Nomenclature. A framework-type describes the connectivity, topology, of the tetrahedrally coordinated atoms constituting the framework, and making an abstraction of the specific properties for those materials. Framework-type zeolite and zeolite-type molecular sieves for which a structure has been established, are assigned a three letter code and are described in the *Atlas of Zeolite Framework Types,* 5th edition, Elsevier, London, England (2001), which is herein fully incorporated by reference.

Non-limiting examples of these molecular sieves include the small pore molecular sieves of a framework-type, e.g., selected from the group consisting of AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves of a framework-type, e.g., selected from the group consisting of AFO, AEL, EUO, HEU, FER, MEL, MFI, MTW, MTT, TON, and substituted forms thereof; and the large pore molecular sieves of a framework-type, e.g., selected from the group consisting of EMT, FAU, and substituted forms thereof. Other suitable molecular sieves can have a different framework-type, e.g., selected from the group consisting of ANA, BEA, CFI, CLO, DON, GIS, LTL, MER, MOR, MWW, and SOD. Non-limiting examples of the preferred molecular sieves, particularly for converting an oxygenate containing feedstock into olefin(s), include those having a framework-type selected from the group consisting of AEL, AFY, BEA, CHA, EDI, FAU, FER, GIS, LTA, LTL, MER, MFI, MOR, MTT, MWW, TAM, and TON. In one preferred embodiment, the molecular sieve of the invention has an AEI topology or a CHA topology, or a combination thereof (e.g., an AEI/CHA intergrowth), and most preferably contains a CHA topology.

Molecular sieve materials all have 3-dimensional, four-connected framework structure of corner-sharing $TO_4$ tetrahedra, where T is any tetrahedrally coordinated cation. These molecular sieves are typically described in terms of the size of the ring that defines a pore, where the size is based on the number of T atoms in the ring. Other framework-type characteristics can include the arrangement of rings that form a cage, and when present, the dimension of channels, and the spaces between the cages. See van Bekkum et al., *Introduction to Zeolite Science and Practice, Second Completely Revised and Expanded Edition,* Volume 137, pages 1-67, Elsevier Science, B.V., Amsterdam, Netherlands (2001).

The small, medium, and large pore molecular sieves typically have from a 4-ring to a 12-ring or greater framework-type. In a preferred embodiment, the zeolitic molecular sieves have 8-, 10-, or 12-ring structures or larger and an average pore size in the range of from about 3 Å to 15 Å. In the most preferred embodiment, the molecular sieves of the invention, preferably silicoaluminophosphate molecular sieves have 8-rings and an average pore size less than about 5 Å, preferably in the range of from 3 Å to about 5 Å, more preferably from 3 Å to about 4.5 Å, and most preferably from 3.5 Å to about 4.2 Å.

Molecular sieves, particularly zeolitic and zeolitic-type molecular sieves, preferably have a molecular framework of one, preferably two or more corner-sharing $[TO_4]$ tetrahedral units, more preferably, two or more $[SiO_4]$, $[AlO_4]$ and/or $[PO_4]$ tetrahedral units. In particularly preferred embodiments, the molecular sieve framework can have two tetrahedral units of $[SiO_4]$ and $[AlO_4]$, or three tetrahedral units of $[SiO_4]$, $[AlO_4]$, and $[PO_4]$. These latter silicon, aluminum, and phosphorous based molecular sieves and metal containing silicon, aluminum and phosphorous based molecular sieves have been described in detail in numerous publications, including, for example, U.S. Pat. No. 4,567,029 (MeAPO where Me is Mg, Mn, Zn, or Co), U.S. Pat. No. 4,440,871 (SAPO), European Patent Application No. EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, and 4,744,885 (FeAPSO), European Patent Application No. EP-A-0 158 975 and U.S. Pat. No. 4,935,216 (ZnAPSO), European Patent Application No. EP-A-0 161 489 (CoAPSO), European Patent Application No. EP-A-0 158 976 (ELAPO, where EL is Co, Fe, Mg, Mn, Ti or Zn), U.S. Pat. No. 4,310,440 ($AlPO_4$), European Patent Application No. EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919 and 4,851,106 (CrAPO), U.S. Pat. Nos. 4,758,419, 4,882,038, 5,434,326, and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956, and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617, and 4,880,520 (TiAPSO), U.S. Pat. Nos. 4,500,651, 4,551,236, and 4,605,492 (TiAPO), U.S. Pat. Nos. 4,824,554 and 4,744,970 (CoAPSO), U.S. Pat. No. 4,735,806 (GaAPSO), European Patent Application No. EP-A-0 293 937 (QAPSO, where Q is framework oxide unit $[QO_2]$), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066, and 5,675,050, all of which are herein fully incorporated by reference.

Where the molecular sieve contains two corner-sharing tetrahedral groups of [SiO$_4$] and [AlO$_4$], the molecular sieve is considered an aluminosilicate. The aluminum to silicon ratio of these aluminosilicates is indicative of the number of acid sites therein. A non-limiting example of aluminosilicates, and their aluminum to silicon ratio, useful in the invention can be found in U.S. Pat. No. 7,094,389, the entire disclosure of which is hereby incorporated be reference.

Other molecular sieves can additionally or alternately include those described in EP-0 888 187 B1 (microporous crystalline metallophosphates, SAPO$_4$ (UIO-6)), U.S. Pat. No. 6,004,898 (molecular sieve and an alkaline earth metal), U.S. patent application Ser. No. 09/511,943 filed Feb. 24, 2000 (integrated hydrocarbon co-catalyst), PCT WO 01/64340 published Sep. 7, 2001 (thorium containing molecular sieve), and R. Szostak, *Handbook of Molecular Sieves*, Van Nostrand Reinhold, New York, N.Y. (1992), which are all herein fully incorporated by reference.

The silicon, aluminum, and/or phosphorous containing molecular sieves, and aluminum, phosphorous, and optionally silicon, containing molecular sieves include aluminophosphate (ALPO) molecular sieves and silicoaluminophosphate (SAPO) molecular sieves and substituted, preferably metal substituted, ALPO and SAPO molecular sieves. One type of particularly preferred molecular sieves is a SAPO molecular sieve, including metal substituted SAPO molecular sieves. In an embodiment, the metal is an alkali metal of Group IA of the Periodic Table of Elements, an alkaline earth metal of Group IIA of the Periodic Table of Elements, a rare earth metal of Group IIIB, including the Lanthamides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, a transition metal of Groups IVB, VB, VIB, VIIB, VIIIB, and IB of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof. In another preferred embodiment, these metal atoms discussed above are inserted into the framework of a molecular sieve through a tetrahedral unit, such as [MeO$_2$], and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the molecular sieve, as described in many of the U.S. patents mentioned above, is represented by the empirical formula, on an anhydrous basis:

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of Al, P and M as tetrahedral oxides, where M is a metal selected from one of Group IA, IIA, IB, IIIB, IVB, VB, VIIB, VIIB, VIIIB and Lanthanide's of the Periodic Table of Elements, preferably M is selected from one of the group consisting of Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01.

In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO and ALPO molecular sieves of the invention include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, ALPO-5, ALPO-11, ALPO-18, ALPO-31, ALPO-34, ALPO-36, ALPO-37, ALPO-46, and metal containing molecular sieves thereof. The more preferred zeolite-type molecular sieves include one or a combination of SAPO-18, SAPO-34, SAPO-35, SAPO-44, SAPO-56, ALPO-18 and ALPO-34, even more preferably one or a combination of SAPO-18, SAPO-34, ALPO-34 and ALPO-18, and metal containing molecular sieves thereof, and most preferably one or a combination of SAPO-34 and ALPO-18, and metal containing molecular sieves thereof.

In an embodiment, the molecular sieve is an intergrowth material having two or more distinct phases of crystalline structures within one molecular sieve composition. In particular, intergrowth molecular sieves are described in the U.S. patent application Ser. No. 09/924,016 filed Aug. 7, 2001 and PCT WO 98/15496 published Apr. 16, 1998, both of which are herein fully incorporated by reference. In another embodiment, the molecular sieve comprises at least one intergrown phase of AEI and CHA framework-types. For example, SAPO-18, ALPO-18 and RUW-18 have an AEI framework-type, and SAPO-34 has a CHA framework-type.

Molecular Sieve Synthesis

The synthesis of molecular sieves is described in many of the references discussed herein. Generally, molecular sieves are synthesized by the hydrothermal crystallization of one or more of a source of aluminum, a source of phosphorous, a source of silicon, a templating agent, and a metal containing compound. Typically, a combination of sources of silicon, aluminum and phosphorous, optionally with one or more templating agents and/or one or more metal containing compounds are placed in a sealed pressure vessel, optionally lined with an inert plastic such as polytetrafluoroethylene, and heated, under a crystallization pressure and temperature, until a crystalline material is formed, and then recovered by filtration, centrifugation and/or decanting.

In one preferred embodiment, the molecular sieves can be synthesized by forming a reaction product of a source of silicon, a source of aluminum, and an organic templating agent, preferably a nitrogen containing organic templating agent. This preferred embodiment results in the synthesis of an aluminosilicate crystalline material that can then be isolated by filtration, centrifugation, and/or decanting.

In another preferred embodiment, the molecular sieves can be synthesized by forming a reaction product of a source of silicon, a source of aluminum, a source of phosphorous, an organic templating agent, preferably a nitrogen containing organic templating agent, and optionally one or more bases (e.g., polymeric). This particularly preferred embodiment results in the synthesis of a silicoaluminophosphate crystalline material that can then be isolated by filtration, centrifugation, and/or decanting.

Non-limiting examples of silicon sources include a silicates, fumed silica, for example, AEROSIL-200 available from Degussa Inc., New York, N.Y., and CAB-O-SIL M-5, silicon compounds such as tetraalkyl orthosilicates, for example, tetramethyl orthosilicate (TMOS) and tetraethylorthosilicate (TEOS), colloidal silicas or aqueous suspensions thereof, for example LUDOX-HS-40 sol available from E.I. du Pont de Nemours, Wilmington, Del., silicic acid, alkali-metal silicate, or any combination thereof. A preferred source of silicon is a silica sol.

Non-limiting examples of aluminum sources include aluminum-containing compositions such as aluminum alkoxides, for example aluminum isopropoxide, aluminum phosphate, aluminum hydroxide, sodium aluminate, pseudo-boehmite, gibbsite and aluminum trichloride, or any combinations thereof. A preferred source of aluminum is pseudo-boehmite, particularly when producing a silicoaluminophosphate molecular sieve.

Non-limiting examples of phosphorous sources, which may also include aluminum-containing phosphorous compositions, include phosphorous-containing, inorganic or organic, compositions such as phosphoric acid, organic phosphates such as triethyl phosphate, and crystalline or amorphous aluminophosphates such as $ALPO_4$, phosphorous salts, or combinations thereof. A preferred source of phosphorous is phosphoric acid, particularly when producing a silicoaluminophosphate.

Templating agents are generally compounds that contain elements of Group VA of the Periodic Table of Elements, particularly nitrogen, phosphorus, arsenic and antimony, more preferably nitrogen or phosphorous, and most preferably nitrogen. Typical templating agents of Group VA of the Periodic Table of elements also contain at least one alkyl or aryl group, preferably an alkyl or aryl group having from 1 to 10 carbon atoms, and more preferably from 1 to 8 carbon atoms. Preferred templating agents typically include nitrogen-containing compounds such as amines and quaternary ammonium compounds.

The quaternary ammonium compounds, in one embodiment, are represented by the general formula $R_4N^+$, where each R is hydrogen or a hydrocarbyl or substituted hydrocarbyl group, preferably an alkyl group or an aryl group having from 1 to 10 carbon atoms. In one embodiment, the templating agents include a combination of one or more quaternary ammonium compound(s) and one or more of a mono-, di- or tri-amine.

Non-limiting examples of templating agents include tetraalkyl ammonium compounds including salts thereof such as tetramethyl ammonium compounds including salts thereof, tetraethyl ammonium compounds including salts thereof, tetrapropyl ammonium including salts thereof, and tetrabutylammonium including salts thereof, cyclohexylamine, morpholine, di-n-propylamine (DPA), tripropylamine, triethylamine (TEA), triethanolamine, piperidine, cyclohexylamine, 2-methylpyridine, N,N-dimethylbenzylamine, N,N-diethylethanolamine, dicyclohexylamine, N,N-dimethylethanolamine, choline, N,N'-dimethylpiperazine, 1,4-diazabicyclo(2,2,2)octane, N',N',N,N-tetramethyl-(1,6) hexanediamine, N-methyldiethanolamine, N-methyl-ethanolamine, N-methyl piperidine, 3-methyl-piperidine, N-methylcyclohexylamine, 3-methylpyridine, 4-methyl-pyridine, quinuclidine, N,N'-dimethyl-1,4-diazabicyclo(2,2,2)octane ion; di-n-butylamine, neopentylamine, di-n-pentylamine, isopropylamine, t-butyl-amine, ethylenediamine, pyrrolidine, and 2-imidazolidone.

One preferred templating agent or template is a tetraethylammonium compound, such as tetraethyl ammonium hydroxide (TEAOH), tetraethyl ammonium phosphate, tetraethyl ammonium fluoride, tetraethyl ammonium bromide, tetraethyl ammonium chloride and tetraethyl ammonium acetate. A preferred templating agent is tetraethyl ammonium hydroxide and salts thereof, particularly when producing a silicoaluminophosphate molecular sieve. In one embodiment, particularly when producing a silicoaluminophosphate molecular sieve, a combination of two or more of any of the above templating agents can be used in combination with one or more of a silicon-, aluminum-, and phosphorous-source, and optionally a polymeric base.

Polymeric bases, when present, especially polymeric bases that are soluble or non-ionic, useful in the invention, can be those having a pH sufficient to control the pH desired for synthesizing a given molecular sieve, especially a SAPO molecular sieve. In a preferred embodiment, when present, the polymeric base can be soluble and/or non-ionic; preferably, the polymeric base, when present, can be a non-ionic and soluble polymeric base, e.g., a polymeric imine such as represented by the following general formula: $(-NHCH_2CH_2-)_m[-N(CH_2CH_2NH_2)CH_2CH_2-]_n)$, where (R—NH) is a polymeric or monomeric unit where R contains from 1 to 20 carbon atoms, preferably from 1 to 10 carbon atoms, more preferably from 1 to 6 carbon atoms, and most preferably from 1 to 4 carbon atoms; x is an integer from 1 to 500,000, where m is from 10 to 20,000, and where n is from 0 to 2,000, preferably from 1 to 2000. In one embodiment, the polymeric base, when present, can have a pH in an aqueous solution, preferably water, from greater than 7 to about 14, more preferably from about 8 to about 14, most preferably from about 9 to 14. In one embodiment, R is a linear, branched, or cyclic polymer, monomeric, chain, preferably a linear polymer chain having from 1 to 20 carbon atoms. In another embodiment, the polymeric base, when present, can be a water miscible polymeric base, preferably in an aqueous solution.

Non-limiting examples of polymer bases include: epichlorohydrin modified polyethylenimine, ethoxylated polyethylenimine, polypropylenimine diamine dendrimers (DAB-Am-n), poly(allylamine) $[CH_2CH(CH_2NH_2)]_n$, poly(1,2-dihydro-2,2,4-trimethylquinoline), and poly(dimethylamine-co-epichlorohydrin-co-ethylenediamine).

In another embodiment, the invention is directed to a method for synthesizing a molecular sieve utilizing a templating agent, preferably an organic templating agent such as an organic amine, an ammonium salt, and/or an ammonium hydroxide, optionally in combination with a polymeric base, such as polyethylenimine.

In a typical synthesis of a SAPO-type molecular sieve, the phosphorous-, aluminum-, and/or silicon-containing components are mixed, preferably while stirring and/or agitation and/or seeding with a crystalline material, optionally with an alkali metal, in a solvent such as water, and with one or more templating agents, to form a synthesis mixture that can then be heated under crystallization conditions of pressure and temperature, as described in U.S. Pat. Nos. 4,440,871, 4,861, 743, 5,096,684, and 5,126,308, which are all herein fully incorporated by reference. The polymeric base, when present, can be combined with the at least one templating agent, and one or more of the aluminum source, phosphorous source, and silicon source, in any order, for example, simultaneously with one or more of the sources, premixed with one or more of the sources and/or templating agent, after combining the sources and the templating agent, and the like.

Generally, the synthesis mixture described above is sealed in a vessel and heated, preferably under autogenous pressure, to a temperature in the range of from about 80° C. to about 250° C., preferably from about 100° C. to about 250° C., more preferably from about 125° C. to about 225° C., even more preferably from about 150° C. to about 180° C. In another embodiment, the hydrothermal crystallization temperature is less than 225° C., preferably less than 200° C. to about 80° C., and more preferably less than 195° C. to about 100° C.

In yet another embodiment, the crystallization temperature can be increased gradually or stepwise during synthesis; preferably the crystallization temperature can be maintained approximately constant for a period of time effective to form a crystalline product. The time required to form the crystalline product can typically be from immediately up to several weeks, the duration of which is usually dependent on the temperature; the higher the temperature, typically the shorter the duration. In one embodiment, the crystalline product can be formed under heating from about 30 minutes to around 2 weeks, preferably from about 45 minutes to about 240 hours, and more preferably from about 1 hour to about 120 hours.

In one embodiment, the synthesis of a molecular sieve can be aided by seeds from another or the same framework type molecular sieve.

The hydrothermal crystallization can be carried out with or without agitation or stirring, for example, stirring or tumbling. The stirring or agitation during the crystallization period may be continuous or intermittent, preferably continuous agitation. Typically, the crystalline molecular sieve product is formed, usually in a slurry state, and can be recovered by any standard technique well known in the art, for example, centrifugation or filtration. The isolated or separated crystalline product, in an embodiment, can be washed, typically using a liquid such as water, from one to many times. The washed crystalline product can then be optionally dried, preferably in air.

One method for crystallization involves forming an aqueous reaction mixture containing an excess amount of a templating agent, subjecting the mixture to crystallization under hydrothermal conditions, establishing an equilibrium between molecular sieve formation and dissolution, and, then, removing some of the excess templating agent to inhibit dissolution of the molecular sieve. See, for example, U.S. Pat. No. 5,296,208, which is herein fully incorporated by reference.

Another method of crystallization is directed to not stirring a reaction mixture, for example a reaction mixture containing at a minimum, a silicon-, aluminum-, and/or phosphorous-containing composition, with a templating agent for a period of time during crystallization. See, for example, International Publication No. WO 01/47810, published Jul. 5, 2001, which is herein fully incorporated by reference.

Other methods for synthesizing molecular sieves or modifying molecular sieves can include, but are not limited to, those described in U.S. Pat. No. 5,879,655 (controlling the ratio of the templating agent to phosphorous), U.S. Pat. No. 6,005,155 (use of a modifier without a salt), U.S. Pat. No. 5,475,182 (acid extraction), U.S. Pat. No. 5,962,762 (treatment with transition metal), U.S. Pat. Nos. 5,925,586 and 6,153,552 (phosphorous modified), U.S. Pat. No. 5,925,800 (monolith supported), U.S. Pat. No. 5,932,512 (fluorine treated), U.S. Pat. No. 6,046,373 (electromagnetic wave treated or modified), U.S. Pat. No. 6,051,746 (polynuclear aromatic modifier), U.S. Pat. No. 6,225,254 (heating template), International Publication No. WO 01/36329 published May 25, 2001 (surfactant synthesis), International Publication No. WO 01/25151 published Apr. 12, 2001 (staged acid addition), International Publication No. WO 01/60746 published Aug. 23, 2001 (silicon oil), U.S. patent application Ser. No. 09/929,949 filed Aug. 15, 2001 (cooling molecular sieve), U.S. patent application Ser. No. 09/615,526 filed Jul. 13, 2000 (metal impregnation including copper), U.S. patent application Ser. No. 09/672,469 filed Sep. 28, 2000 (conductive microfilter), and U.S. patent application Ser. No. 09/754,812 filed Jan. 4, 2001 (freeze drying the molecular sieve), which are all herein fully incorporated by reference.

In one preferred embodiment, when a templating agent is used in the synthesis of a molecular sieve, it is preferred that the templating agent be substantially, preferably completely, removed after crystallization by numerous well known techniques, for example, heat treatments such as calcination. Calcination involves contacting the molecular sieve containing the templating agent with a gas, preferably containing oxygen, at any desired concentration and at an elevated temperature sufficient to either partially or completely decompose and/or oxidize the templating agent.

Molecular sieves can have either a high silicon (Si) to aluminum (Al) ratio or a low silicon to aluminum ratio; however, a low Si/Al ratio is typically preferred for SAPO synthesis. In one embodiment, the molecular sieve has a Si/Al ratio less than 0.65, preferably less than 0.40, more preferably less than 0.32, and most preferably less than 0.20. In another embodiment the molecular sieve has a Si/Al ratio in the range of from about 0.65 to about 0.10, preferably from about 0.40 to about 0.10, more preferably from about 0.32 to about 0.10 or from about 0.32 to about 0.15.

The pH of a reaction mixture containing at a minimum a silicon-, aluminum-, and/or phosphorous-containing composition, and a templating agent, should be in the range of from 2 to 10, preferably in the range of from 4 to 9, and most preferably in the range of from 5 to 8. The pH can be controlled by the addition of basic or acidic compounds as necessary to maintain the pH during the synthesis, for example, in the preferred range of from 4 to 9. In another embodiment, the templating agent and/or base, if necessary, can be added to the reaction mixture (e.g., of the silicon source and phosphorous source) such that the pH of the reaction mixture does not exceed 10.

In one embodiment, the molecular sieves of the invention can be combined with one or more other molecular sieves. In another embodiment, the silicoaluminophosphate or aluminophosphate molecular sieves, or a combination thereof, can be combined with one more of the following non-limiting examples of molecular sieves, described in the following references: Beta (U.S. Pat. No. 3,308,069), ZSM-5 (U.S. Pat. Nos. 3,702,886, 4,797,267, and 5,783,321), ZSM-11 (U.S. Pat. No. 3,709,979), ZSM-12 (U.S. Pat. No. 3,832,449), ZSM-12 and ZSM-38 (U.S. Pat. No. 3,948,758), ZSM-22 (U.S. Pat. No. 5,336,478), ZSM-23 (U.S. Pat. No. 4,076,842), ZSM-34 (U.S. Pat. No. 4,086,186), ZSM-35 (U.S. Pat. No. 4,016,245, ZSM-48 (U.S. Pat. No. 4,397,827), ZSM-58 (U.S. Pat. No. 4,698,217), MCM-1 (U.S. Pat. No. 4,639,358), MCM-2 (U.S. Pat. No. 4,673,559), MCM-3 (U.S. Pat. No. 4,632,811), MCM-4 (U.S. Pat. No. 4,664,897), MCM-5 (U.S. Pat. No. 4,639,357), MCM-9 (U.S. Pat. No. 4,880,611), MCM-10 (U.S. Pat. No. 4,623,527), MCM-14 (U.S. Pat. No. 4,619,818), MCM-22 (U.S. Pat. No. 4,954,325), MCM-41 (U.S. Pat. No. 5,098,684), M-41S (U.S. Pat. No. 5,102,643), MCM-48 (U.S. Pat. No. 5,198,203), MCM-49 (U.S. Pat. No. 5,236,575), MCM-56 (U.S. Pat. No. 5,362,697), ALPO-11 (U.S. Pat. No. 4,310,440), titanium aluminosilicates (TASO), TASO-45 (European Patent Application No. EP-A-0 229 295), boron silicates (U.S. Pat. No. 4,254,297), titanium aluminophosphates (TAPO) (U.S. Pat. No. 4,500,651), mixtures of ZSM-5 and ZSM-11 (U.S. Pat. No. 4,229,424), ECR-18 (U.S. Pat. No. 5,278,345), SAPO-34 bound ALPO-5 (U.S. Pat. No. 5,972,203), International Publication No. WO 98/57743 published Dec. 23, 1988 (molecular sieve and Fischer-Tropsch), U.S. Pat. No. 6,300,535 (MFI-bound zeolites), and mesoporous molecular sieves (U.S. Pat. Nos.

6,284,696, 5,098,684, 5,102,643, and 5,108,725), which are all herein fully incorporated by reference.

Method for Making Molecular Sieve Catalyst Compositions

Once the molecular sieve is synthesized, depending on the requirements of the particular conversion process, the molecular sieve can then be formulated into a molecular sieve catalyst composition, particularly for commercial use. The molecular sieves synthesized above can be made or formulated into catalysts by combining the synthesized molecular sieves with a binder and/or a matrix material to form a molecular sieve catalyst composition or a formulated molecular sieve catalyst composition. This formulated molecular sieve catalyst composition can typically be formed into particles of useful shape and size by well-known techniques such as spray drying, pelletizing, extrusion, and the like.

There are many different binders that can be useful in forming the molecular sieve catalyst composition. Non-limiting examples of binders that are useful alone or in combination include various types of hydrated alumina, silicas, and/or other inorganic oxide sol. One preferred alumina containing sol is aluminum chlorhydrol. The inorganic oxide sol acts like glue binding the synthesized molecular sieves and other materials such as the matrix together, particularly after thermal treatment. Upon heating, the inorganic oxide sol, preferably having a low viscosity, can be converted into an inorganic oxide matrix component. For example, an alumina sol will typically convert to an aluminum oxide matrix following heat treatment.

Aluminum chlorhydrol, a hydroxylated aluminum based sol containing a chloride counter ion, has the general formula of $Al_mO_n(OH)_oCl_p \cdot x(H_2O)$ wherein m is 1 to 20, n is 1 to 8, o is 5 to 40, p is 2 to 15, and x is 0 to 30. In one embodiment, the binder is $Al_{13}O_4(OH)_{24}Cl_7 \cdot 12(H_2O)$ as is described in G. M. Wolterman et al., *Stud. Surf. Sci. and Catal.*, 76, pages 105-144 (1993), which is herein incorporated by reference. In another embodiment, one or more binders can be combined with one or more other non-limiting examples of alumina materials, such as aluminum oxyhydroxide, γ-alumina, boehmite, diaspore, and transitional aluminas such as α-alumina, β-alumina, γ-alumina, δ-alumina, ε-alumina, κ-alumina, and ρ-alumina, aluminum trihydroxide, and/or other aluminas such as gibbsite, bayerite, nordstrandite, doyelite, and mixtures thereof.

In another embodiment, the binders can be alumina sols, predominantly comprising aluminum oxide, optionally including some silicon. In yet another embodiment, the binders can be peptized alumina made by treating alumina hydrates, such as pseudoboehmite, with an acid, preferably an acid that does not contain a halogen, to prepare sols or aluminum ion solutions. Non-limiting examples of commercially available colloidal alumina sols include NALCO 8676, available from Nalco Chemical Co., Naperville, Ill., and NYACOL, available from The PQ Corporation, Valley Forge, Pa.

The molecular sieve synthesized above, in a preferred embodiment, can be combined with one or more matrix materials. Matrix materials are typically effective in reducing overall catalyst cost, acting as thermal sinks assisting in shielding heat from the catalyst composition for example during regeneration, densifying the catalyst composition, increasing catalyst strength such as crush strength and attrition resistance, and controlling the rate of conversion in a particular process.

Non-limiting examples of matrix materials include one or more of: rare earth metals, metal oxides including titania, zirconia, magnesia, thoria, beryllia, quartz, silica or sols, and mixtures thereof, for example, silica-magnesia, silica-zirconia, silica-titania, silica-alumina, and silica-alumina-thoria, and the like. In an embodiment, matrix materials include natural clays, such as those from the families of montmorillonite and/or kaolin. These natural clays can include, but are not limited to, subbentonites and those kaolins known as, for example, Dixie, McNamee, Georgia, and Florida clays. Non-limiting examples of other matrix materials include: haloysite, kaolinite, dickite, nacrite, and anauxite. In one embodiment, the matrix material, preferably any of the clays, can be subjected to well known modification processes, such as calcination, acid treatment, and/or chemical treatment.

In one preferred embodiment, the matrix material is a clay or clay-type composition, preferably having a low iron or titanium content; in one preferred embodiment, the matrix material comprises, preferably is, kaolin. Kaolin has been found to form a pumpable, high-solid-content slurry; it has a low fresh surface area; and it packs together easily, presumably due to its platelet structure. A preferred average particle size of the matrix material, preferably kaolin, can be from about 0.1 μm to about 0.6 μm, with a particle size distribution such that $d_{90}$ (i.e., the average particle size, or diameter, of 90% of the particles) can preferably be less than about 1 μm.

In one embodiment, the binder, the molecular sieve, and the matrix material can be combined in the presence of a liquid to form a molecular sieve catalyst composition, where the amount of binder can be from about 2% by weight to about 30% by weight, preferably from about 5% by weight to about 20% by weight, and more preferably from about 7% by weight to about 15% by weight, based on the total weight of the binder, the molecular sieve, and matrix material, excluding the liquid (after calcination).

In another embodiment, the weight ratio of the binder to the matrix material used in the formation of the molecular sieve catalyst composition can be from 0:1 to 1:15, preferably 1:15 to 1:5, more preferably 1:10 to 1:4, and most preferably 1:6 to 1:5. It has been found that a higher sieve content, lower matrix content, can increase certain aspects of the molecular sieve catalyst composition performance; however, lower sieve content, higher matrix content, can improve the attrition resistance of the composition.

Upon combining the molecular sieve and the matrix material, optionally with a binder, in a liquid to form a slurry, mixing, preferably rigorous mixing, is typically needed to produce a substantially homogeneous mixture containing the molecular sieve. Non-limiting examples of suitable liquids include one or a combination of water, alcohol, ketones, aldehydes, and/or esters. The most preferred liquid comprises, or is, water. In one embodiment, the slurry can be colloid-milled for a period of time sufficient to produce the desired slurry texture, sub-particle size, and/or sub-particle size distribution.

The molecular sieve and matrix material, and the optional binder, can be in the same or different liquid, and can be combined in any order—together, simultaneously, sequentially, or a combination thereof. In a preferred embodiment, the same liquid, preferably water, can be used. The molecular sieve, matrix material, and optional binder, can be combined with the liquid as solids, substantially dry or in a dried form, or as slurries, together or separately. If solids are added together as dry or substantially dried solids, it is preferable to add a limited and/or controlled amount of liquid.

In one embodiment, the slurry of the molecular sieve, binder, and matrix materials can be mixed or milled to achieve a sufficiently uniform slurry of sub-particles of the molecular sieve catalyst composition, that can then be fed to a forming unit to produce the molecular sieve catalyst composition. In a preferred embodiment, the forming unit comprises spray dryer. Typically, the forming unit is maintained at a temperature sufficient to remove at least most of the liquid from the slurry, and from the resulting molecular sieve catalyst composition. The resulting catalyst composition, when formed in this way, can take the form of microspheres.

When a spray drier comprises the forming unit, typically, the slurry of the molecular sieve and matrix material, and optionally a binder, can be co-fed to the spray drying volume with a drying gas with an average inlet temperature ranging from 200° C. to 550° C., and a combined outlet temperature ranging from 100° C. to about 225° C. In an embodiment, the average diameter (particle size) of the spray dried formed catalyst composition is from about 40 μm to about 300 μm, preferably from about 50 μm to about 250 μm, more preferably from about 50 μm to about 200 μm, and most preferably from about 65 μm to about 90 μm.

During spray drying, the slurry can be passed through a nozzle distributing the slurry into small droplets, resembling an aerosol spray into a drying chamber. Atomization can be achieved by forcing the slurry through a single nozzle or through multiple nozzles with a pressure drop in the range of from 100 psia to 1000 psia (690 kPaa to 6900 kPaa). In another embodiment, the slurry can be co-fed through a single nozzle or through multiple nozzles along with an atomization fluid, such as air, steam, flue gas, or any other suitable gas.

In yet another embodiment, the slurry described above can be directed to the perimeter of a spinning wheel that distributes the slurry into small droplets, the size of which can be controlled by many factors, including slurry viscosity, surface tension, flow rate, pressure, and temperature of the slurry, the shape and dimension of the nozzle(s), and/or the spinning rate of the wheel. These droplets can then be dried in a co-current or counter-current flow, e.g. of air, passing through a spray drier to form a substantially dried or dried molecular sieve catalyst composition, more specifically a molecular sieve catalyst composition in powder form.

Generally, the size of the powder can be controlled to some extent by the solids content of the slurry. However, control of the size of the catalyst composition and its spherical characteristics can be attained by varying the slurry feed properties and conditions of atomization.

Other methods for forming a molecular sieve catalyst composition are described in U.S. patent application Ser. No. 09/617,714 filed Jul. 17, 2000 (spray drying using a recycled molecular sieve catalyst composition), which is herein incorporated by reference.

In another embodiment, the formulated molecular sieve catalyst composition can contain from about 1% to about 99%, more preferably from about 5% to about 90%, and most preferably from about 10% to about 80%, by weight of the molecular sieve based on the total weight of the molecular sieve catalyst composition.

In another embodiment, the weight percent of binder in or on the spray dried molecular sieve catalyst composition, based on the total weight of the binder, molecular sieve, and matrix material, can be from about 2% by weight to about 30% by weight, preferably from about 5% by weight to about 20% by weight, and more preferably from about 7% by weight to about 15% by weight.

Once the molecular sieve catalyst composition is formed in a substantially dry or dried state, to further harden and/or activate the formed catalyst composition, a heat treatment such as calcination, at an elevated temperature is usually performed. A conventional calcination environment comprises air, which typically includes a small amount of water vapor. Typical calcination temperatures can be in the range from about 400° C. to about 1,000° C., preferably from about 500° C. to about 800° C., and most preferably from about 550° C. to about 700° C., preferably in a calcination environment such as air, nitrogen, helium, flue gas (combustion product lean in oxygen), or any combination thereof.

In one embodiment, calcination of the formulated molecular sieve catalyst composition can be carried out in any number of well known devices, including rotary calciners, fluid bed calciners, batch ovens, and the like. Calcination time can typically depend on the degree of hardening of the molecular sieve catalyst composition and the temperature ranges from about 15 minutes to about 2 hours.

In a preferred embodiment, the molecular sieve catalyst composition can be heated in nitrogen at a temperature of from about 600° C. to about 700° C. Heating can be carried out for a period of time, typically from 30 minutes to 15 hours, preferably from 1 hour to about 10 hours, more preferably from about 1 hour to about 5 hours, and most preferably from about 2 hours to about 4 hours.

Other methods for activating a molecular sieve catalyst composition, in particular where the molecular sieve is a reaction product of the combination of silicon-, phosphorous-, and aluminum-containing sources, and a templating agent, more particularly a silicoaluminophosphate catalyst composition (SAPO), are described, for example, in U.S. Pat. No. 5,185,310 (heating molecular sieve of gel alumina and water to 450° C.), International Publication No. WO 00/75072 published Dec. 14, 2000 (heating to leave an amount of template), and U.S. application Ser. No. 09/558,774 filed Apr. 26, 2000 (rejuvenation of molecular sieve), which are all herein fully incorporated by reference.

Oxygenate to Olefins Process

The method of the present invention is conducted in a reactor apparatus. As used herein, the term "reactor apparatus" refers to an apparatus which includes at least a place in which an oxygenate to olefin conversion reaction takes place. As further used herein, the term "reaction zone" refers to the portion of a reactor apparatus in which the oxygenate to olefin conversion reaction takes place and can be used synonymously with the term "reactor." Desirably, the reactor apparatus can include a reaction zone, an inlet zone, and a disengaging zone. The "inlet zone" is the portion of the reactor apparatus into which feed and catalyst are introduced. The "reaction zone" is the portion of the reactor apparatus in which the feed is contacted with the catalyst under conditions effective to convert the oxygenate portion of the feed into a light olefin product. The "disengaging zone" is the portion of the reactor apparatus in which the catalyst and any additional solids in the reactor are separated from the products. Typically, the reaction zone is positioned between the inlet zone and the disengaging zone.

In a preferred embodiment of the process of the invention, the feedstock contains one or more oxygenates, more specifically, one or more organic compound(s) containing at least one oxygen atom. In the most preferred embodiment of the process of invention, the oxygenate in the feedstock is one or more alcohols, preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include, but are not limited to, lower straight and branched chain aliphatic alcohols and their unsaturated counterparts. Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof.

In the most preferred embodiment, the feedstock can be selected from one or more of methanol, ethanol, dimethyl ether, diethyl ether, and a combination thereof, more preferably comprising methanol and/or dimethyl ether, and most preferably comprising methanol.

The various feedstocks discussed above, particularly a feedstock containing an oxygenate, more particularly a feedstock containing an alcohol, can be converted primarily into one or more olefins. The olefin(s) or olefin monomer(s) produced from the feedstock typically have from 2 to 30 carbon atoms, preferably 2 to 8 carbon atoms, more preferably 2 to 6 carbon atoms, still more preferably 2 to 4 carbons atoms, and most preferably include ethylene and/or propylene.

Non-limiting examples of olefin monomer(s) include ethylene, propylene, butene-1, pentene-1,4-methyl-pentene-1, hexene-1, octene-1, and decene-1, preferably ethylene, propylene, butene-1, pentene-1,4-methyl-pentene-1, hexene-1, octene-1, and isomers thereof. Other olefin monomer(s) can include unsaturated monomers, diolefins having 4 to 18 carbon atoms, conjugated or nonconjugated dienes, polyenes, vinyl monomers, and cyclic olefins.

In the most preferred embodiment, the feedstock, preferably of one or more oxygenates, can be converted in the presence of a molecular sieve catalyst composition into one or more olefins having 2 to 6 carbons atoms, preferably 2 to 4 carbon atoms. Most preferably, the one or more olefins, alone or in combination, can be converted from a feedstock containing an oxygenate, preferably an alcohol, most preferably methanol, to one or more of the preferred olefins, ethylene and/or propylene.

The feedstock, in one embodiment, contains one or more diluents, typically used to reduce the concentration of the feedstock, and which are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, propane, and the like), essentially non-reactive aromatic compounds, and mixtures thereof. The most preferred diluents include water and nitrogen, with water being particularly preferred.

The diluent, in the case of water, can be used in a liquid form, a vapor form, or a combination thereof. The diluent can be added directly to a feedstock entering into a reactor, directly into a reactor, and/or along with a molecular sieve catalyst composition. In one embodiment, the amount of diluent in the feedstock can be in the range of from about 1 to about 99 mole percent, based on the total number of moles of the feedstock and diluent, preferably from about 1 to 80 mole percent, more preferably from about 5 to about 50, most preferably from about 5 to about 25. In one embodiment, other hydrocarbons can be added to a feedstock either directly or indirectly, and can include olefin(s), paraffin(s), aromatic(s) (see for example U.S. Pat. No. 4,677,242), or mixtures thereof, preferably propylene, butylene, pentylene, and other hydrocarbons having 4 or more carbon atoms, or mixtures thereof.

The process for converting a feedstock, especially a feedstock containing one or more oxygenates, in the presence of a molecular sieve catalyst composition of the invention, can be carried out in a reactor, where the reaction process can include a fixed bed process or a fluidized bed process, preferably a continuous fluidized bed process.

The reaction processes can take place in a variety of catalytic reactors such as hybrid reactors that have a dense bed or fixed bed zones and/or fast fluidized bed reaction zones coupled together, circulating fluidized bed reactors, riser reactors, and the like. Suitable conventional reactor types are described in, for example, U.S. Pat. No. 4,076,796, U.S. Pat. No. 6,287,522, and *Fluidization Engineering*, D. Kunii and O. Levenspiel, Robert E. Krieger Publishing Company, New York, N.Y. 1977, which are all herein fully incorporated by reference.

The preferred reactor type are riser reactors generally described in *Riser Reactor, Fluidization and Fluid-Particle Systems*, pages 48 to 59, F. A. Zenz and D. F. Othmo, Reinhold Publishing Corporation, New York, 1960, and U.S. Pat. No. 6,166,282, and U.S. patent application Ser. No. 09/564,613 filed May 4, 2000, which are all herein fully incorporated by reference.

A preferred embodiment of a reactor system for the present invention is a circulating fluid bed reactor with continuous regeneration.

In a preferred embodiment, a fluidized bed process or high velocity fluidized bed process can include a reactor apparatus, regeneration system, and recovery system.

In one embodiment of the present invention, if the reactor is a high velocity fluidized bed reactor (referred to herein as a riser reactor), above about 2 meters per second gas superficial velocity, then a portion of the catalyst exiting from the disengaging zone can be returned, or recirculated, to the reaction zone, becoming recirculated catalyst. This is different from a typical Fluid Catalytic Cracker (FCC) riser reactor, where all or most of the catalyst exiting the top of the reactor and entering the disengaging zone is sent to the regenerator. The return, or recirculation, of coked catalyst directly to the reactor, without regenerating the coked catalyst, allows the average coke level in the reactor to build up to a preferred level. By adjusting the ratio of the flow of the coked catalyst from the disengaging zone to the regenerator and the reactor, a preferred level of carbon atoms per acid site of the molecular sieves of the catalyst particles can be maintained in the reactor apparatus, including on this recirculated catalyst.

In another embodiment of the present invention, if the fluidized bed reactor is designed with low superficial gas velocities, below about 2 m/sec, then cyclones may be used to return catalyst fines to the fluidized bed reaction zone. Such reactors generally have high recirculation rates of solids within the fluidized bed, which can allow the coke level on the catalyst to build to a preferred level. Desirable average coke loading can be maintained by withdrawing catalyst from the bed and regenerating the catalyst in the manner described above, and then returning at least a portion of this regenerated catalyst to the reactor.

A preferred embodiment of a reactor apparatus comprising a riser for use in the present invention is depicted generally as 10 in FIG. 1. A methanol feed passed through line 12 is at least partially vaporized in a preheater (not shown). The methanol feed is mixed with regenerated catalyst from line 28 and coked catalyst from line 22 at the bottom of the riser reactor 14. An inert gas and/or steam may be used to dilute the methanol, lift the catalyst streams in line 28, provide fluidization to the catalyst stream in line 22 and keep pressure instrument lines clear of catalyst. This inert gas and/or steam mixes with the methanol and catalyst in the riser reactor 14. The reaction is exothermic, and the preferred reaction temperature, in the range of from about 300° C. to about 500° C., is maintained by removing heat. Heat can be removed by any suitable means, including but not necessarily limited to cooling the reactor with a catalyst cooler (not shown), feeding some of the methanol as a liquid, cooling the catalyst feed to the reactor, or any combination of these methods.

The reactor effluent flowing through the reactor exit 16 of riser reactor 14, containing products, coked catalyst, diluents, and unconverted feed, should flow to a disengaging zone 18. In the disengaging zone 18, coked catalyst is separated from the gaseous materials by means of gravity and/or cyclone separators. A portion of the coked catalyst in line 22 is recirculated to the reactor inlet at the bottom of riser reactor 14. The portion of coked catalyst from line 22 to be regenerated is first sent to a stripping zone 29, where steam or other inert gas is used to recover adsorbed hydrocarbons from the catalyst. Stripped spent coked catalyst via line 23 flows to the regenerator 24. The portion of the catalyst sent to the regenerator 24 should be contacted with a regeneration medium, preferably a gas comprising oxygen, via line 30 introduced through regeneration medium inlet 31, at temperatures, pressures, and residence times that are capable of burning coke off of the molecular sieve-containing catalyst and down to a level of no greater than 10 carbon atoms, say less than 3, 2, or even 1 carbon atom(s) per acid site of the molecular sieve.

The preferred temperature in the regenerator can be in the range of from about 550° C. to about 700° C.; the preferred oxygen concentration in the gas leaving the regenerator can be in the range of from about 0.1 vol % to about 5 vol %; and the preferred residence time can be in the range of from about 1 to about 100 minutes.

The burning off of coke is exothermic. The temperature may be maintained at a suitable level by any acceptable method, including but not limited to feeding cooler gas, cooling the catalyst in the regenerator with a cat cooler 26, or a combination of these methods.

The regenerated catalyst is sent via line 28 to the reactor 14, where it mixes with the recirculated coked catalyst from line 22 and the methanol feed from line 12. The regenerated catalyst in line 28 may be lifted to the reactor 14 by means of an inert gas, steam, or methanol vapor introduced via a lift gas line (not shown). The process should repeat itself in a continuous or semi-continuous manner. The hot reactor product gases exiting via line 20 should be cooled, the water byproduct condensed and collected, and the desired olefin product gases recovered for further processing.

In an embodiment, the amount of liquid feedstock fed, separately or jointly with a vapor feedstock, to a reactor system can be in the range of from 0.1 weight percent to about 85 weight percent, preferably from about 1 weight percent to about 75 weight percent, more preferably from about 5 weight percent to about 65 weight percent, based on the total weight of the feedstock including any diluent contained therein. The liquid and vapor feedstocks can preferably be of similar composition, or can contain varying proportions of the same or different feedstock, with the same or different diluent.

The feedstock entering the fluidized bed reactor apparatus is preferably converted, partially or fully, in the reaction zone into a gaseous effluent that enters the disengaging zone along with a coked molecular sieve catalyst composition. In the preferred embodiment, cyclone(s) within the disengaging vessel are designed to separate the molecular sieve catalyst composition, preferably a coked molecular sieve catalyst composition, from the gaseous effluent containing one or more olefins within the disengaging zone. Cyclones are preferred; however, gravity effects within the disengaging vessel will typically also separate the catalyst compositions from the gaseous effluent. Other methods for separating the catalyst compositions from the gaseous effluent include the use of plates, caps, elbows, and the like.

In one embodiment of the disengaging zone, the disengaging zone includes a disengaging vessel, typically a lower portion of which disengaging vessel comprises a stripping zone. In the stripping zone, the coked molecular sieve catalyst composition can be contacted with a gas, preferably one or a combination of steam, methane, carbon dioxide, carbon monoxide, hydrogen, and an inert gas such as argon, more preferably comprising steam, to recover adsorbed hydrocarbons from the coked molecular sieve catalyst composition that can then be introduced to the regeneration system. In another embodiment, the stripping zone can be in a separate vessel from the disengaging vessel, with the gas typically being passed at a gas hourly superficial velocity (GHSV) of from 1 $hr^{-1}$ to about 20,000 $hr^{-1}$, based on the volume of gas to volume of coked molecular sieve catalyst composition, preferably at an elevated temperature from 250° C. to about 750° C., more preferably from about 350° C. to 650° C., over the coked molecular sieve catalyst composition.

The conversion temperature employed in the conversion process, specifically within the reactor system, can be in the range of from about 200° C. to about 1000° C., preferably from about 250° C. to about 800° C., more preferably from about 250° C. to about 750° C., yet more preferably from about 300° C. to about 650° C., yet even more preferably from about 350° C. to about 600° C., and most preferably from about 350° C. to about 550° C.

The conversion pressure employed in the conversion process, specifically within the reactor system, can vary over a wide range, including autogenous pressure. The conversion pressure is generally based on the partial pressure of the feedstock, exclusive of any diluent therein. Typically, the conversion pressure employed in the process can be in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock, excluding any diluents, to the reaction zone per hour per weight of molecular sieve in the molecular sieve catalyst composition in the reaction zone. The WHSV can advantageously be maintained at a level sufficient to keep the catalyst composition in a fluidized state within a reactor.

Typically, the WHSV can range from about 1 $hr^{-1}$ to about 5000 $hr^{-1}$, preferably from about 2 $hr^{-1}$ to about 3000 $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment, the WHSV can be greater than 20 $hr^{-1}$. Preferably, the WHSV for conversion of a feedstock containing methanol and dimethyl ether can be in the range of from about 20 $hr^{-1}$ to about 300 $hr^{-1}$.

The superficial gas velocity (SGV) of the feedstock, including diluent and reaction products within the reactor system, can preferably be sufficient to fluidize the molecular sieve catalyst composition within a reaction zone in the reactor. The SGV in the process, particularly within the reactor system, more particularly within the riser reactor(s), can be at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See, for example, U.S. patent application Ser. No. 09/708,753 filed Nov. 8, 2000, which is herein incorporated by reference.

In one preferred embodiment of the process for converting an oxygenate to olefin(s) using a silicoaluminophosphate molecular sieve catalyst composition, the process can be operated at a WHSV of at least 20 $hr^{-1}$ and a Temperature Corrected Normalized Methane Selectivity (TCNMS) of less than 0.016, preferably less than or equal to 0.01. See, for example, U.S. Pat. No. 5,952,538, which is herein fully incorporated by reference.

In another embodiment of the processes for converting an oxygenate such as methanol to one or more olefins using a molecular sieve catalyst composition, the WHSV can be from 0.01 hr$^{-1}$ to about 100 hr$^{-1}$, with a temperature of from about 350° C. to 550° C., and a silica to Me$_2$O$_3$ (Me is a Group IIIA or VIII element from the Periodic Table of Elements, e.g., aluminum) molar ratio of from 300 to 2500. See, for example, European Patent Application No. EP-0 642 485 B1, which is herein fully incorporated by reference.

Other processes for converting an oxygenate such as methanol to one or more olefins using a molecular sieve catalyst composition are described in International Publication No. WO 01/23500 published Apr. 5, 2001, which is herein incorporated by reference.

The conversion of oxygenates to light olefins can be catalyzed by various molecular sieve catalysts. During conversion, carbonaceous deposits known as "coke" unavoidably form on the surface of or within (pores of) the molecular sieve catalyst. In order to avoid a significant reduction in catalyst activity, the catalyst can typically be regenerated by burning off coke deposits.

In an embodiment, a portion of the coked molecular sieve catalyst composition can be withdrawn from the reactor apparatus and introduced to the regeneration system. The regeneration system comprises a regenerator, where the coked catalyst composition can be contacted with a regeneration medium, preferably a gas containing oxygen, under conditions of temperature, pressure, and residence time typical for such regeneration.

Non-limiting examples of the regeneration medium include one or more of oxygen, O$_3$, SO$_3$, N$_2$O, NO, NO$_2$, N$_2$O$_5$, air, air diluted with nitrogen or carbon dioxide, oxygen and water (U.S. Pat. No. 6,245,703), carbon monoxide, and/or hydrogen. The regeneration conditions are typically those capable of burning coke from the coked catalyst composition, preferably to a coke level less than 0.5 weight percent, based on the total weight of the coked molecular sieve catalyst composition, to form a regenerated molecular sieve catalyst composition.

The regeneration temperature can be in the range of from about 200° C. to about 1500° C., preferably from about 300° C. to about 1000° C., more preferably from about 450° C. to about 750° C., and most preferably from about 550° C. to 700° C. The regeneration pressure can be in the range of from about 15 psia (100 kPaa) to about 500 psia (3.4 MPaa), preferably from about 20 psia (140 kPaa) to about 250 psia (1.7 MPaa), more preferably from about 25 psia (170 kPaa) to about 150 psia (1 MPaa), and most preferably from about 30 psia (210 kPaa) to about 60 psia (414 kPaa).

The preferred residence time of the molecular sieve catalyst composition in the regenerator can be in the range of from about one minute to several hours, most preferably about one minute to 100 minutes, and the preferred volume of oxygen in the gas can be in the range of from about 0.01 mole percent to about 5 mole percent, based on the total volume of the gas.

In one embodiment, regeneration promoters, typically metal containing compounds such as platinum, palladium, and the like, can be added to the regenerator directly, or indirectly, for example, with the coked catalyst composition. Also, in another embodiment, a fresh molecular sieve catalyst composition can be added to the regenerator containing a regeneration medium of oxygen and water, as described in U.S. Pat. No. 6,245,703, which is herein fully incorporated by reference.

In an embodiment, a portion of the regenerated molecular sieve catalyst composition from the regenerator can be returned to the reactor apparatus, or directly to the reaction zone, or indirectly, by pre-contacting with the feedstock, or contacting with fresh molecular sieve catalyst composition, or contacting with a regenerated molecular sieve catalyst composition or a cooled regenerated molecular sieve catalyst composition described below.

The burning of coke is an exothermic reaction, and, in an embodiment, the temperature within the regeneration system can be controlled by various techniques in the art, including feeding a cooled gas to the regenerator vessel, operated in a batch, continuous, or semi-continuous mode, or a combination thereof. A preferred technique involves withdrawing the regenerated molecular sieve catalyst composition from the regeneration system and passing the regenerated molecular sieve catalyst composition through a catalyst cooler that forms a cooled regenerated molecular sieve catalyst composition. The catalyst cooler, in an embodiment, comprises a heat exchanger that is located either internal or external to the regeneration system.

In one embodiment, the cooled regenerated molecular sieve catalyst composition can be returned to the regenerator in a continuous cycle; alternatively, (see U.S. patent application Ser. No. 09/587,766 filed Jun. 6, 2000) one portion of the cooled regenerated molecular sieve catalyst composition can be returned to the regenerator vessel in a continuous cycle, and another portion of the cooled molecular sieve regenerated molecular sieve catalyst composition can be returned to the reaction zone, directly or indirectly, or a portion of the regenerated molecular sieve catalyst composition or cooled regenerated molecular sieve catalyst composition can be contacted with by-products within the gaseous effluent (see International Publication No. WO 00/49106 published Aug. 24, 2000), which are all herein fully incorporated by reference. In another embodiment, a regenerated molecular sieve catalyst composition contacted with an alcohol, preferably ethanol, 1-propanol, 1-butanol, or mixture thereof, can be introduced to the reactor system, as described in U.S. patent application Ser. No. 09/785,122 filed Feb. 16, 2001, which is herein fully incorporated by reference.

Other methods for operating a regeneration system are disclosed in U.S. Pat. No. 6,290,916, which is herein fully incorporated by reference.

In one embodiment, the regenerated molecular sieve catalyst composition withdrawn from the regeneration system, preferably from the catalyst cooler, can be combined with a fresh molecular sieve catalyst composition and/or recirculated molecular sieve catalyst composition and/or feedstock, and returned to the reactor apparatus. In another embodiment, the regenerated molecular sieve catalyst composition withdrawn from the regeneration system can be returned to the reaction zone, optionally after passing through a catalyst cooler. In one embodiment, a carrier, such as an inert gas, feedstock vapor, steam, or the like, semi-continuously or continuously, can facilitate the introduction of the regenerated molecular sieve catalyst composition to the reaction zone.

In one embodiment, the gaseous effluent can be withdrawn from the disengaging zone and passed through a recovery system. There are many well known recovery systems, techniques, and sequences that can be useful in separating olefins and purifying olefins from gaseous effluents. Recovery systems generally comprise one or more, or a combination, of various separation, fractionation, and/or distillation towers, columns, and splitters, and other associated equipment, for example, various condensers, heat exchangers, refrigeration systems or chill trains, compressors, knock-out drums or pots, pumps, and the like.

Non-limiting examples of these towers, columns, splitters, and trains, used alone or in combination, include one or more of a demethanizer, preferably a high temperature demethanizer, a deethanizer, a depropanizer, preferably a wet depropanizer, a wash tower often referred to as a caustic wash tower and/or quench tower, absorbers, adsorbers, membranes, ethylene (C2) splitter, propylene (C3) splitter, butene (C4) splitter, and the like.

Various recovery systems useful for recovering predominately olefins, preferably prime or light olefins such as ethylene and propylene (and sometimes also butene) are described in U.S. Pat. Nos. 5,960,643, 5,019,143, 5,452,581, 5,082,481, 5,672,197, 6,069,288, 5,904,880, 5,927,063, 6,121,504, 6,121,503, and 6,293,998, which are all herein fully incorporated by reference.

Generally, accompanying most recovery systems is the production, generation, and/or accumulation of additional products, by-products, and/or contaminants, along with the preferred products. The preferred products, typically the prime/light olefins, such as ethylene and propylene, are typically purified for use in derivative manufacturing processes such as oligomerization processes, polymerization processes, and the like. Therefore, in the most preferred embodiment of the recovery system, the recovery system can also include a purification system. For example, the light olefins produced particularly in a MTO process can be passed through a purification system that removes low levels of by-products/contaminants.

Non-limiting examples of contaminants and by-products include generally polar compounds such as water, alcohols, carboxylic acids, ethers, carbon oxides, sulfur compounds such as hydrogen sulfide, carbonyl sulfides, and mercaptans, ammonia and other nitrogen compounds, arsine, phosphine, and chlorides, inter alia. Other contaminants or by-products can include, but are not limited to, hydrogen and hydrocarbons such as acetylene, methyl acetylene, propadiene, butadiene, and butyne.

Other recovery systems that include purification systems, for example for the purification of olefins, are described in *Kirk-Othmer Encyclopedia of Chemical Technology*, 4th Edition, Volume 9, John Wiley & Sons, 1996, pages 249-271 and 894-899, which is herein incorporated by reference. Purification systems are also described in, for example, U.S. Pat. No. 6,271,428, U.S. Pat. No. 6,293,999, and U.S. patent application Ser. No. 09/689,363 filed Oct. 20, 2000, which are herein incorporated by reference.

In one way to determine the carbon atoms per acid site of the molecular sieve component of the catalyst, it is first necessary to determine the acid site density of the molecular sieve by a suitable analytic method, e.g., by NMR, and then determine the coke content of the catalyst by conventional methods, e.g., by burning off coke to form oxides of carbon, the extent of which can be measured by a suitable analytic method, e.g., IR spectroscopy.

The acid site density of the catalyst can range from 0.10 mmol/g to 0.40 mmol/g of formulated catalyst, e.g., from 0.13 mmol/g to 0.38 mmol/g of formulated catalyst or from 0.20 mmol/g to 0.30 mmol/g of formulated catalyst.

The acidity desired for a specific organic conversion catalyst can be based upon various factors, including but not limited to the type of the reactor in which conversion takes place, intended operating conditions for the reactor, and feedstock characteristics. Acidity of the catalyst is of particular interest in oxygenates to olefins conversion, inasmuch as excessive acidity can cause premature coking of the catalyst.

For silicoaluminophosphate molecular sieve materials, acidity is typically directly related to the ratio of silicon atoms to aluminum atoms in the framework. Acidity for aluminosilicate molecular sieve materials, e.g., zeolites, can be inversely related to the ratio of silicon atoms to aluminum atoms. Thus, one way to attain a desired acidity for molecular sieve materials can be by altering synthesis protocols, e.g., by adjusting the ratio of silicon atoms to aluminum atoms in the synthesis mixture. Desired acid site densities for molecular sieve materials can be achieved in other ways as well, including the substitution of an ion (e.g., an $H^+$ ion) associated with an acid site with another ion (e.g., a metal ion).

Because the catalyst is typically regenerated relatively frequently, the reactor apparatus can advantageously allow easy removal of a portion of the catalyst to a regenerator, where the catalyst can be subjected to a regeneration medium, preferably a gas comprising oxygen, most preferably air, to burn off coke from the catalyst, which can at least partially restore catalyst activity. The conditions of temperature, oxygen partial pressure, and residence time in the regenerator can be selected to achieve an average coke loading on regenerated catalyst, e.g., commensurate with Eqn. 1 below. At least a portion of the regenerated catalyst should be returned to the reactor apparatus, or more particularly the reaction zone, optionally through some portion of the reactor apparatus or through combination with a recirculated catalyst, as described herein. In various other embodiments, at least a portion of the regenerated catalyst can be returned to the reactor apparatus having an average coke loading as determined using the following equation:

Optimal Coke on catalyst at Max POS=(C per Acid Site at Max POS)*(Sieve ASD)*12*(Wt % Sieve in Catalyst)/1000   Eqn. 1 where Max POS represents a maximum in prime/light olefin (ethylene and/or propylene) selectivity, Sieve ASD represents the acid site density of the molecular sieve, and the number of carbons per acid site at Max POS is determined by the equation:

C per acid site at max POS=−51.226*[Si/Al$_2$ in Sieve]+25.777   Eqn. 2

It is recognized that the molecular sieve catalyst composition in the reaction zone is made up of a mixture of regenerated catalyst and catalyst having varying levels of carbonaceous deposits. The measured coke level of carbonaceous deposits thus represents an average of the levels of individual catalyst particles. In an embodiment of the present invention, the reactor apparatus of the process is operated such that a certain average coke loading on the catalyst, comprising a mixture of both regenerated and unregenerated catalyst particles, is maintained in the reactor apparatus. More particularly, in the reaction zone, an average coke loading can be maintained such that the molecular sieve-containing catalyst particles in the reactor apparatus or reaction zone have an average coke loading determined by the above equations.

Average coke levels on the molecular sieve catalyst composition can be measured, e.g., by withdrawing the molecular sieve catalyst composition from the conversion process at some point, and then by determining the catalyst's carbon content.

In order to determine the loading of coke in the reactor and/or in the regenerator, small aliquots of catalyst may be continuously or periodically withdrawn or directly sampled from one or more appropriate points in the reactor apparatus, e.g., the reaction zone or disengaging zone or any catalyst recirculation pathway present (exclusive of the regenerated catalyst pathway). In one embodiment, illustrated in FIG. 1, the catalyst recirculation pathway can be defined as the path through riser 14 through line 16 to the disengaging zone 18, thence through line 22, returning via line 28 to the riser 14.

In one embodiment of the present invention, average coke level can be determined by measurement via infrared spectroscopy of oxides of carbon produced by combustion of coke on catalyst. Average coke loading, in terms of carbon atoms per acid site on the molecular sieve of the catalyst, can then be determined from the average coke level by reference to determination of acid sites in the molecular sieve by a suitable technique, e.g., NMR determination of acid site density. The process controls may be adjusted accordingly to provide desired average coke loading, e.g., by controlling the amount of addition of regenerated catalyst from the regeneration zone to the reaction zone, and/or by controlling the regeneration conditions and thus extent to which coke is removed during regeneration.

Control of the coke loading can be carried out in several ways, including partial or full regeneration of a slipstream of coked catalyst that takes into account the size of the slipstream relative to the entire catalyst inventory and the amount of coke removed during regeneration. For example, see the method of Lattner et al., in U.S. Pat. No. 6,023,005, which is incorporated herein by reference.

In one embodiment, the desired average coke loading on the molecular sieve catalyst composition in the reaction zone can be maintained by controlling the flow of the regenerated molecular sieve catalyst composition or cooled regenerated molecular sieve catalyst composition from the regeneration system to the reactor system, and from regenerator to reactor. Techniques for controlling the flow of a molecular sieve catalyst composition are described in Michael Louge, *Experimental Techniques, Circulating Fluidized Beds*, Grace, Avidan and Knowlton, eds., Blackie, 1997 (336-337), which is herein incorporated by reference.

The product olefin(s), particularly the light olefins of ethylene and propylene, can be polymerized to form plastic compositions, e.g., polyolefins, particularly polyethylene and polypropylene. Any of a variety of processes for forming polyethylene or polypropylene can be used. Catalytic processes are preferred, in some cases. In one preferred embodiment, the catalytic polymerization process can involve one or more of metallocene, Ziegler/Natta, aluminum oxide, and acid catalytic systems. In general, these methods involve contacting the ethylene or propylene product with a polyolefin-forming catalyst at a pressure and temperature effective to form the polyolefin product.

In another embodiment, the product olefin(s), particularly the light olefins of ethylene and propylene, can either homopolymerized or copolymerized with one or more other monomers.

In an embodiment, the olefin product can be separated into components (e.g., into ethylene and propylene), one or more of which can be contacted with a metallocene catalyst to form a polymer product such as a polyolefin. Preferably, the polyolefin forming process can be carried out at a temperature ranging between about 50° C. and about 320° C. The reaction can be carried out at low, medium, or high pressure, being anywhere within the range of about 1 barg (100 kPag) to about 3200 barg (320 MPag). For processes carried out in solution, an inert diluent can be used. In this type of operation, it is preferred that the pressure be at a range of from about 10 barg (1 MPag) to about 150 barg (15 MPag), and also preferably at a temperature range of from about 120° C. to about 250° C. For gas-phase processes, it is preferred that the temperature generally be within a range of about 60° C. to 120° C. and that the operating pressure be from about 5 barg (500 kPag) to about 50 barg (5 MPag).

In addition to polyolefins, numerous other olefin derivatives may be formed from the ethylene, propylene, and $C_{4+}$ olefins, particularly butylene, separated according to this invention. The olefins separated according to this invention can also be used in the manufacture of such compounds as aldehydes, acids such as $C_2$-$C_{13}$ mono carboxylic acids, alcohols such as $C_2$-$C_{12}$ mono alcohols, esters made from the $C_2$-$C_{12}$ mono carboxylic acids and the $C_1$-$C_{12}$ mono alcohols, linear alpha olefins, vinyl acetate, ethylene dichloride and vinyl chloride, ethylbenzene, ethylene oxide, cumene, acrolein, allyl chloride, propylene oxide, acrylic acid, ethylene-propylene rubbers, acrylonitrile, and trimers and dimers of ethylene and propylene. The $C_{4+}$ olefins, butylenes in particular, are particularly suited for the manufacture of aldehydes, acids, alcohols, and esters made from $C_5$-$C_{13}$ mono carboxylic acids.

Additionally or alternately, the present invention can relate to the following list of embodiments:

Embodiment 1. A process for converting oxygenates to olefins comprising the steps of: a) contacting a feed comprising an oxygenate with a catalytically effective amount of molecular sieve catalyst under conditions effective to selectively convert at least some of the oxygenate to a product comprising prime olefins and depositing a certain amount of coke on the catalyst, the catalyst having an $Si/Al_2$ value, a maximum POS, and an active fraction comprising a number of acid sites; and b) optimizing the POS by adjusting the amount of coke present relative to the number of acid sites contained in the active fraction of the catalyst.

Embodiment 2. The process of embodiment 1, wherein the optimizing step comprises determining the number of carbon atoms per acid site at maximum POS.

Embodiment 3. The process of embodiment 2, wherein the number of carbon atoms per acid site at maximum POS is determined by NMR.

Embodiment 4. The process of embodiment 2, wherein the number of carbon atoms per acid site at maximum POS is determined by estimation.

Embodiment 5. The process of any of the previous embodiments, wherein the optimizing step comprises determining a ratio necessary to achieve an optimum POS using the equation: carbon atoms per acid site at maximum POS=−51.226*[Si/Al2 in sieve]+25.777.

Embodiment 6. The process of embodiment 5, wherein the optimizing step further comprises adjusting the amount of coke present on the coked catalyst relative to the carbon atoms per acid sites at maximum POS calculated using the equation.

Embodiment 7. A method for optimizing a coke level for catalysts with different acidity levels comprising the steps of: a) contacting a feed comprising an oxygenate with a catalytically effective amount of molecular sieve catalyst under conditions effective to selectively convert at least some oxygenate to a product comprising prime olefins and depositing an amount of coke on the catalyst, the catalyst having an active fraction comprising a number of acid sites at maximum product selectivity; b) determining the number of carbon atoms per acid site at maximum product selectivity; c) determining a ratio necessary to achieve an optimum selectivity to the product using the equation: carbon atoms per acid site at maximum product selectivity=−51.226*[Si/Al2 in sieve]+25.777; and d) adjusting the amount of coke present on the coked catalyst relative to the carbon atoms per acid sites at maximum product selectivity calculated in step (c).

Embodiment 8. The method of embodiment 7, wherein the carbon atoms per acid site at maximum product selectivity is calculated by NMR or elemental analysis.

Embodiment 9. The method of embodiment 7 or 8, wherein the amount of coke present on the coked catalyst is adjusted to a level below 0.5 wt % coke on catalyst by full regeneration of the coked catalyst.

Embodiment 10. The method of any of embodiments 7-9, wherein the amount of coke present on the coked catalyst is adjusted to a level of at least 0.5 wt % coke on catalyst by at least partial regeneration of the coked catalyst.

Embodiment 11. The method of any of embodiments 7-10, wherein the product comprises a light olefin.

Embodiment 12. The method of any of embodiments 7-11, wherein the bound molecular sieve catalyst is a SAPO catalyst.

Embodiment 13. The method of any of embodiments 7-12, wherein the bound molecular sieve catalyst comprises ALPO-18, ALPO-34, SAPO-17, SAPO-18, SAPO-34, a substituted group thereof, or a combination thereof.

Embodiment 14. The method of embodiment 13, wherein the bound molecular sieve catalyst comprises SAPO 34.

Embodiment 15. The method of any of embodiments 7-14, wherein the bound molecular sieve catalyst has a framework-type of at least one selected from the group consisting of AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted groups thereof.

Embodiment 16. The method of any of embodiments 7-15, further comprising the step of operating an oxygenates-to-olefins conversion reactor in such a way as to load an optimum amount of coke on a catalyst, based on an acid site density of the catalyst, to achieve a prime olefin selectivity of at least within 3% of an optimum prime olefin selectivity.

Embodiment 17. A process for forming a polymer product from an olefin product comprising one or more prime olefin monomers, the process comprising: a) providing an olefin product formed according to the process/method of any of the previous embodiments, which comprises one or more prime olefin monomers; and b) contacting at least one of the prime olefin monomers, and optionally one or more comonomers, with a catalytically effective amount of a polymerization catalyst under conditions sufficient to polymerize the olefin product and optional comonomer(s).

Embodiment 18. A process for forming an oligomer product from an olefin product comprising one or more prime olefin monomers, the process comprising: a) providing an olefin product formed according to the process/method of any of the previous embodiments, which comprises one or more prime olefin monomers; and b) contacting at least one of the prime olefin monomers, and optionally one or more comonomers, with a catalytically effective amount of an oligomerization catalyst under conditions sufficient to oligomerize the olefin product and optional comonomer(s).

EXAMPLES

Aspects of the present invention can be further described in the following examples, which are intended merely to illustrate the invention and not to limit its scope, as defined by the appended claims.

SAPO-34 was prepared in accordance with the method set out in U.S. Pat. No. 4,440,871, incorporated herein by reference. Two different samples with slightly different acid densities were prepared. Catalyst One contained a molecular sieve which was an intergrowth of SAPO-34 and SAPO/ALPO-18 and exhibited an acid site density of 0.13 mmol H+/g formulated catalyst. Catalyst Two, containing a nearly pure SAPO-34, exhibited a higher acid density than Catalyst One, namely 0.38 mmol H+/g formulated catalyst. Acid site density was measured by magic angle spinning solid state proton NMR (MAS SS $^1$H NMR) in accordance with the procedure set out below.

Acid Site Density Measurement

The acid site density of bound, or formulated, catalysts typically reflects the relative contributions of the sieve, binder, and matrix/filler used to formulate the catalyst. It is believed that the binder and matrix/filler used to formulate the MTO catalyst does not contribute significantly to the MTO conversion activity, and so these components have effectively zero acid site density. Therefore, comparisons herein will be made using the Acid Site Density of the molecular sieve in the sample.

Sample Preparation for NMR measurements: Prior to the NMR measurements, SAPO-34 samples were calcined in air at about 650° C., packed in 4 mm (o.d.) $ZrO_2$ Bruker MAS rotors, evacuated at about 400° C. for about 10 hrs, then capped under $N_2$.

Experimental NMR Parameters: 360.13 MHz $^1$H MAS NMR spectra were obtained on the Bruker AMX360 wide bore spectrometer with a 4 mm MAS probe using 10.0 kHz spinning, 3.0 μs 90° pulses, and a 30 s pulse delay; 32 scans were collected for each spectrum. The proportions of each proton species in each sample was determined by directly comparing the experimental spectral area relative to that of the quantitation standard and weight normalizing. The standards and the samples were run back to back under identical conditions to minimize any effects due to the spectrometer instability. The spectrometer tuning was not changed from sample to sample, or from sample to standard. A full rotor of octakis(trimethylsiloxy)silesquioxane, more commonly known as Q8M8, available from Strem Chemicals (CAS# 51777-38-9) was used as the external quantitation standard. It is a solid at room temperature, has similar tuning characteristics to SAPOs, and exhibits one peak at about 0.3 ppm from TMS (tetramethylsilane). Measurements done in quadruplicate on similar systems gave a standard deviation of <4% for this methodology.

A series of active materials was generated with varying acid site densities. Acid site density (ASD) in SAPO molecular sieves can be measured directly by NMR or can be calculated from the atomic $Si/Al_2$ ratios, e.g., by using elemental analysis of the sieve. From Equation 3, the acid site density (ASD) of a sample of SAPO sieve can be calculated from the elemental analysis:

$$\text{Acid site density (ASD in mmol/g)} = (Si/Al_2/0.334) * 1.37 \text{ mmol/g} \qquad \text{Eqn 3}$$

Average Coke Loading Measurement

Coke level was measured with a LECO analyzer, Model C-200. The analyzer essentially burns the carbonaceous species and analyzes the off gas. In dividing the amount of carbon observed in the off gas by the weight of the sample analyzed, the carbon loading on the catalyst as a percentage can be determined. Any other species (e.g., hydrogen) not observed with the LECO analyzer were assumed to be absent and are therefore not included quantitatively in coke level measurements/determinations.

When performing a coke level measurement, the crucible and crucible lid were removed from a nitrogen-purged dry box. Approximately 0.8 grams of iron chip accelerator and 1.3 grams of copper accelerator (both supplied by LECO Corporation) were blended in the crucible with roughly 0.2 grams of catalyst. Zero grade oxygen which had been filtered by an anhydrone (magnesium perchlorate, supplied by LECO) and a $CO_2$ absorber (sodium hydroxide on a non-fibrous silicate carrier, also from LECO) were passed over the heated catalyst sample. The catalyst was heated with an induction furnace. CO and $CO_2$ were evolved and passed through the anhydrone and were then sent through a bed of platinum on alumina obtained from LECO. This bed oxidized substantially all the CO to $CO_2$. The resulting gas was passed through an infrared detector where $CO_2$ was detected. The IR detector was calibrated using two standard samples—3.31 wt % carbon (carbon and sulfur in white iron, supplied by LECO) and 6.17 wt % carbon (tungsten carbide, also from LECO).

The mass of carbon detected by the IR cell can be divided by the catalyst weight to determine the coke level as a percentage. Having already determined the acid site density, e.g., by the NMR method detailed above, and also coke level, the average number of carbon atoms per acid site (also termed average coke loading) was determined according to the following equation:

C atoms/site=(coke level [g/g])/(molecular weight [g/mol])/(acid density [moles/g]).

Methanol to olefin experiments were conducted in a fluidized bed reactor, as set out in FIG. 1, where distilled methanol was reacted with formulated SAPO-34 catalyst. Methanol, fed mostly as a vapor, contacted the catalyst cocurrently at the bottom of the reactor. The energy of the gas, due to its velocity, carried the catalyst out of the riser and into a cyclone train. The gas was separated from the catalyst in the cyclones. At the solids discharge from the cyclone(s), most of the catalyst was recirculated to the reactor again, while a small portion (about 5%) was sent to a regenerator. Coke on the catalyst was burned to reactivate the catalyst. The regenerated catalyst was then returned to the reactor catalyst recirculation loop. The average coke loading on the catalyst in the riser was controlled by controlling regeneration conditions (e.g., oxygen content in regeneration medium, temperature, average residence time, etc.).

The experiments were conducted at constant pressure, temperature, and conversion with varying average coke loadings. As the average coke loading increased, catalyst reactivity to methanol decreased. Therefore, space velocity was varied simultaneously with average coke loading, such that conversion at the outlet of the reactor could be held constant. More precisely, the space velocity was decreased as average coke loading was increased, so that total reactor activity could be held constant. Coke level can be reported (1) as the mass of carbon divided by the total mass of catalyst, and/or (2) as the average number of carbon atoms deposited divided by the number of catalytic acid sites (or average coke loading). Coke (carbon) deposition was measured by burning off the carbon from a reactor catalyst sample and measuring the amount of $CO_x$ that evolved using a LECO Model C-200. For each test, conditions were held constant at about 98% reactor outlet conversion in the reactor, about 488° C. average riser temperature, and about 276 kPa (25 psig) riser outlet pressure. Space velocity was reported as the ratio of methanol feed to (1) the mass of catalyst in the riser, and/or (2) the number of acid sites in the reactor. A summary of the test results is set out in Table 1 below.

Table 1 below also shows the $Si/Al_2$ ratio and Acid Site Density of the sieve for a series of catalyst samples, some of which were formulated and others of which were not. The $Si/Al_2$ ratios for the sieves below ranged from about 0.12 to about 0.22, which covers a range of catalyst acidities.

TABLE 1

| Example | Catalyst type | Sieve Type | wt % sieve | $Si/Al_2$ ratio in sieve | Sieve ASD (mmol H+/g) |
| --- | --- | --- | --- | --- | --- |
| 1 | SAPO | Sieve | 100% | 0.120 | 0.49 |
| 2 | SAPO | Sieve | 100% | 0.143 | 0.58 |
| 3 | SAPO | Sieve | 100% | 0.170 | 0.70 |
| 4 | SAPO | Sieve | 100% | 0.170 | 0.70 |
| 5 | SAPO | Sieve | 100% | 0.220 | 0.90 |
| 6 | SAPO | Bound | 40% | 0.120 | 0.49 |
| 7 | SAPO | Bound | 40% | 0.153 | 0.63 |
| 8 | SAPO | Bound | 40% | 0.160 | 0.66 |

The catalysts shown in Table 1 were tested for MTO performance in a laboratory scale device known as a 50× Unit. The 50× is an automated, continuous flow test reactor in which a small amount of bound or unbound catalyst is mixed with 100 mg of SiC diluent, heated in an electric clam-shell heater, and exposed to a flow of pre-vaporized methanol. Periodically, gas phase samples in the effluent stream are captured and analyzed via an FID-equipped GC to determine conversion and gas phase product yields.

The results showed that the coke selectivity (which is used to calculate coke yield) can be calculated using a hydrogen balance approach (i.e., the deviation from the methanol feed H/C ratio can be used to closely estimate the buildup of H-deficient coke on the catalyst balanced against the higher H content saturates in the product stream).

In these experiments, a total of 15 gas samples were collected for each of the catalysts in Table 1 at typical conditions used to measure MTO performance. The gas samples were analyzed by GC to determine the time on stream performance of a given catalyst. By integrating the calculated coke yield, the build up of coke on catalyst can be determined at the time on stream corresponding to each GC analyzed sample. For the catalysts listed in Table 1, the prime olefin selectivity (POS) vs. coke on catalyst (or sieve, as appropriate) is shown as FIG. 2.

Figure 2:
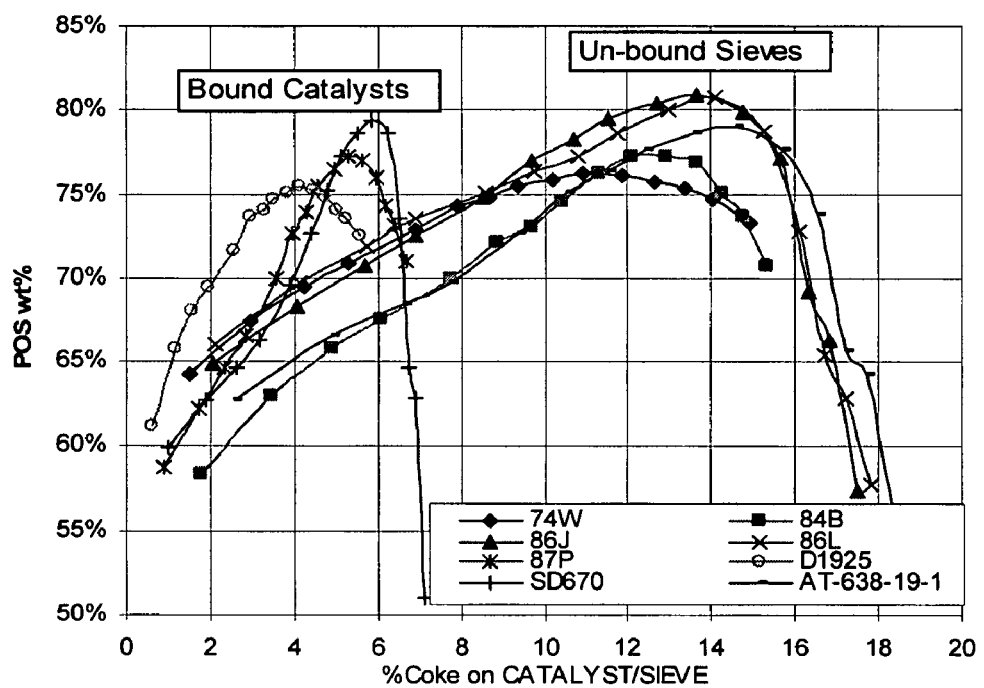
FIG. 2 illustrates the Prime Olefin Selectivity (POS) vs Coke on Catalyst for various catalysts at about 475° C., about 100 WHSV (sieve), and about 25 psig.

In FIG. 2, two features are immediately evident. First of all, the value of coke at which the POS reaches a maximum varies considerably based on the level of sieve in the catalyst sample (40 wt % for bound catalyst, and 100 wt % for unbound sieve). An operator of an MTO unit could have difficulty in readily predicting the optimal coke level to operate the unit with a given catalyst, and determination of the optimum by trial and error could be time consuming and expensive. Second of all, generally, but not always, the value of POS at the maximum value increases with increasing coke on catalyst.

These observations are quantified below in Table 2 by looking at Max POS and wt % Coke on Sieve at Max POS. As stated previously, laboratory work has shown that the binder and filler used to formulate MTO catalysts do not contribute significantly to the MTO conversion activity of formulated or bound catalysts. Furthermore, at the coke levels shown in FIG. 2, there is believed to be no appreciable coke accumulation on the binder or filler; rather, the coke is believed to be accumulated within the pore structure of the active sieve component of the catalyst. Therefore, Coke on Sieve can be calculated from the measured coke on catalyst and the known content of sieve in the formulated catalyst. The final column of Table 2 shows the number of C atom per Sieve Acid Site at Max POS (abbreviated as C/Site) using Eqn. 4:

$$\text{C/Site (mmol/mmol)} = (\text{Wt \% Coke on Sieve}/(12*1000))/\text{mmol [H+]/g} \quad \text{Eqn. 4}$$

where mmol [H+]/g is the same as the ASD shown in Table 1.

The C/Site column in Table 2 clearly shows that the optimal coke level for different catalysts varies with Acid Site Density. If the optimal coke level did not vary with Acid Site Density, all of the catalysts would have had the same value for C/Site at Max POS, but this is obviously not the case.

Figure 3A:
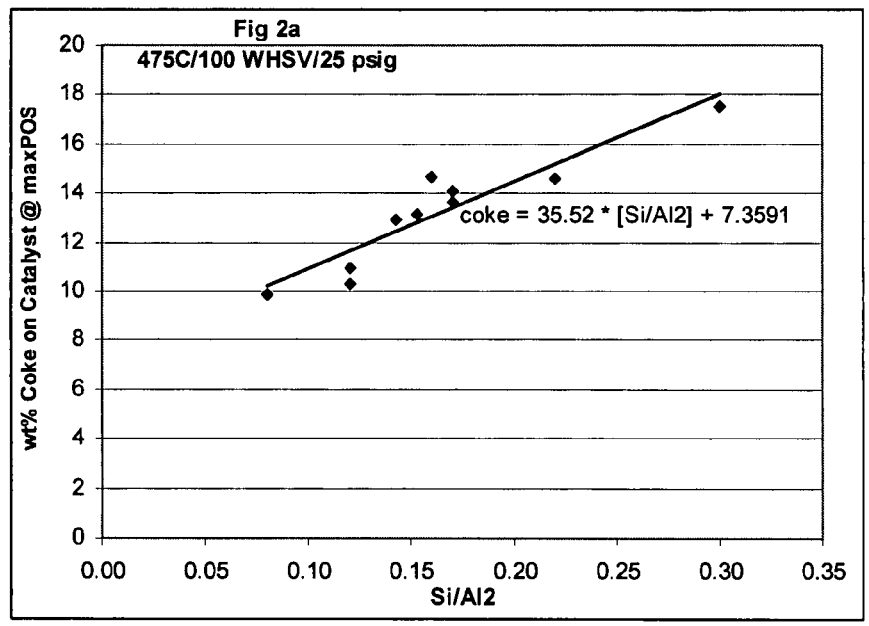
FIG. 3a illustrates the values of optimal coke loadings as measured by Wt % Coke on Sieve.
Figure 3B:
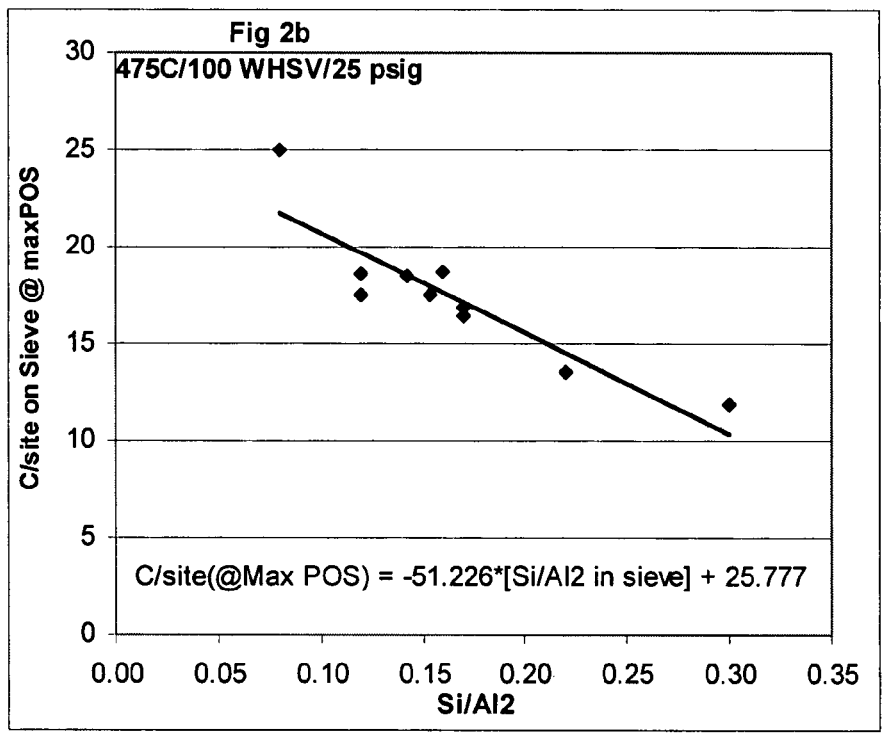
FIG. 3b shows that the amount of carbon per acid site needed to achieve optimum POS decreases with increasing acidity (as described by Si/Al$_2$).

FIG. 3a shows graphically the data presented in Table 2 and illustrates that, for these samples, the values of optimal coke loadings, as measured by Wt % Coke on Sieve, increase with increasing sieve acidity (as described by $Si/Al_2$ ratio). On the other hand, FIG. 3b shows that the amount of carbon per acid site needed to achieve optimum POS decreases with increasing acidity (again as described by $Si/Al_2$). These relationships thus teach how to select the optimum coke loadings for a wide range of catalyst acidity levels.

TABLE 2

| Example | Catalyst Type | Sieve Type | wt % sieve | Si/Al$_2$ in sieve | mmol H+/g | Max POS | wt % Coke on Bound Cat At Max POS | wt % Coke on Sieve at Max POS | C/Site At Max POS |
|---|---|---|---|---|---|---|---|---|---|
| 1 | SAPO | Sieve | 100% | 0.120 | 0.49 | 76.2 | N/A | 10.9 | 18.5 |
| 2 | SAPO | Sieve | 100% | 0.143 | 0.58 | 77.3 | N/A | 12.9 | 18.4 |
| 3 | SAPO | Sieve | 100% | 0.170 | 0.70 | 80.8 | N/A | 14.1 | 16.8 |
| 4 | SAPO | Sieve | 100% | 0.170 | 0.70 | 80.9 | N/A | 13.7 | 16.3 |
| 5 | SAPO | Sieve | 100% | 0.220 | 0.90 | 79.1 | N/A | 14.6 | 13.5 |
| 6 | SAPO | Bound | 40% | 0.120 | 0.49 | 75.4 | 4.1 | 10.3 | 17.4 |
| 7 | SAPO | Bound | 40% | 0.153 | 0.63 | 77.2 | 5.3 | 13.2 | 17.5 |
| 8 | SAPO | Bound | 40% | 0.160 | 0.66 | 79.4 | 5.9 | 14.7 | 18.6 |

Table 2 and FIGS. 3*a* and 3*b* describe the point optima for coke loadings that should yield approximately optimum POS at varying acidity levels. In practice, slightly sub-optimum POS values may be desirable in some instances for other reasons. For example, even though lower than optimal coke loadings can generate less than optimum POS, it may be desirable to operate with those loadings, e.g., in order to improve the activity of the coked catalysts. Similarly, it may, in other cases, be advantageous to operate with higher than optimal coke loadings, e.g., in order to increase the POR (ethylene to propylene ratio). The current invention provides a method of accomplishing these goals while still being able to achieve a near-optimum POS.

Table 3a illustrates the methodology for doing so. A series of coke loadings on the catalyst, both above and below an optimal coke loading, are defined in which the POS is within 1% and 3% (absolute) of the calculated optimal POS. Thus, the pairs of values listed in the last four columns of Table 3a represent the lower and upper limits on coke loading on the catalyst as a function of acid site density, to achieve a product slate within 1% of the optimum and 3% of the optimum, respectively. Table 3b shows the same data, but the last four columns are expressed in terms of C atoms/ASD (mmol/mmol), where ASD refers to Acid Site Density of the sieve used in the catalyst.

TABLE 3a

| Ex. | Catalyst Type | Sieve Type | Si/Al$_2$ in sieve | mmol H+/g | wt % Coke on Bound Cat @ Max POS | wt % Coke on Sieve at Max POS | wt % Coke on catalyst @1% off POS Max | | wt % Coke on catalyst @3% off POS Max | |
|---|---|---|---|---|---|---|---|---|---|---|
| | | | | | | | Lower bound | Upper Bound | Lower Bound | Upper Bound |
| 1 | SAPO | Sieve | 0.120 | 0.49 | N/A | 10.9 | 9.4 | 13.2 | 7.0 | 15.0 |
| 2 | SAPO | Sieve | 0.143 | 0.58 | N/A | 12.9 | 11.5 | 14.0 | 10.4 | 14.5 |
| 3 | SAPO | Sieve | 0.170 | 0.70 | N/A | 14.1 | 12.0 | 14.8 | 10.7 | 15.3 |
| 4 | SAPO | Sieve | 0.170 | 0.70 | N/A | 13.7 | 13.8 | 14.8 | 11.3 | 15.3 |
| 5 | SAPO | Sieve | 0.220 | 0.90 | N/A | 14.6 | 12.8 | 15.5 | 11.0 | 16.2 |
| 6 | SAPO | Bound | 0.120 | 0.49 | 4.1 | 10.3 | 3.2 | 4.6 | 2.7 | 5.6 |
| 7 | SAPO | Bound | 0.153 | 0.63 | 5.3 | 13.2 | 4.8 | 5.8 | 4.2 | 6.2 |
| 8 | SAPO | Bound | 0.160 | 0.66 | 5.9 | 14.7 | 5.4 | 6.3 | 5.0 | 6.4 |

TABLE 3b

| Ex. | Catalyst Type | Sieve Type | Si/Al$_2$ in sieve | mmol H+/g | wt % Coke on Bound Cat @ Max POS | wt % Coke on Sieve at Max POS | C/Site @ −1% off POS Max | | C/Site @ −3% off POS Max | |
|---|---|---|---|---|---|---|---|---|---|---|
| | | | | | | | Lower bound | Upper Bound | Lower bound | Upper Bound |
| 1 | SAPO | Sieve | 0.120 | 0.49 | N/A | 10.9 | 15.9 | 22.3 | 11.9 | 25.4 |
| 2 | SAPO | Sieve | 0.143 | 0.58 | N/A | 12.9 | 16.4 | 20.0 | 14.8 | 20.7 |
| 3 | SAPO | Sieve | 0.170 | 0.70 | N/A | 14.1 | 14.3 | 17.7 | 12.8 | 18.3 |
| 4 | SAPO | Sieve | 0.170 | 0.70 | N/A | 13.7 | 16.5 | 17.7 | 13.5 | 18.3 |
| 5 | SAPO | Sieve | 0.220 | 0.90 | N/A | 14.6 | 11.8 | 14.3 | 10.2 | 15.0 |
| 6 | SAPO | Bound | 0.120 | 0.49 | 4.1 | 10.3 | 5.4 | 7.8 | 4.6 | 9.5 |
| 7 | SAPO | Bound | 0.153 | 0.63 | 5.3 | 13.2 | 6.4 | 7.7 | 5.6 | 8.2 |
| 8 | SAPO | Bound | 0.160 | 0.66 | 5.9 | 14.7 | 6.9 | 8.0 | 6.3 | 8.0 |

What is claimed is:

1. A process for forming a polymer product from an olefin product comprising one or more prime olefin monomers, the process comprising:
   a. providing an olefin product formed by a process comprising the steps of;
      (i) contacting a feed comprising an oxygenate with a catalytically effective amount of molecular sieve catalyst under conditions effective to selectively convert at least some of the oxygenate to a product comprising prime olefins and depositing a certain amount of coke on the catalyst, the catalyst having an $Si/Al_2$ value, a maximum POS, and an active fraction comprising a number of acid sites;
      (ii) optimizing the POS by adjusting the amount of coke present relative to the number of acid sites contained in the active fraction of the catalyst; and
   b. contacting at least one of the prime olefin monomers, and optionally one or more comonomers, with a catalytically effective amount of a polymerization catalyst under conditions sufficient to polymerize the olefin product and optional comonomer(s); wherein the optimizing step comprises determining a ratio necessary to achieve an optimum POS using the equation: carbon atoms per acid site at maximum POS=$-51.226*[Si/Al_2$ in sieve]+ 25.777.

2. A process for forming an oligomer product from an olefin product comprising one or more prime olefin monomers, the process comprising:
   c. providing an olefin product formed by a process comprising the steps of;
      (i) contacting a feed comprising an oxygenate with a catalytically effective amount of molecular sieve catalyst under conditions effective to selectively convert at least some of the oxygenate to a product comprising prime olefins and depositing a certain amount of coke on the catalyst, the catalyst having an $Si/Al_2$ value, a maximum POS, and an active fraction comprising a number of acid sites;
      (ii) optimizing the POS by adjusting the amount of coke present relative to the number of acid sites contained in the active fraction of the catalyst; and
   d. contacting at least one of the prime olefin monomers, and optionally one or more comonomers, with a catalytically effective amount of an oligomerization catalyst under conditions sufficient to oligomerize the olefin product and optional comonomer(s); wherein the optimizing step comprises determining a ratio necessary to achieve an optimum POS using the equation: carbon atoms per acid site at maximum POS=$-51.226*[Si/Al_2$ in sieve]+ 25.777.

3. The process of claim 1 or 2, wherein the optimizing step further comprises adjusting the amount of coke present on the coked catalyst relative to the carbon atoms per acid sites at maximum POS calculated using the equation.

* * * * *